US012271799B2

(12) United States Patent
Ruple et al.

(10) Patent No.: US 12,271,799 B2
(45) Date of Patent: Apr. 8, 2025

(54) TECHNIQUES FOR DISEASE PREDICTION USING MACHINE LEARNING-IMPROVED SIMULATIONS AND FOR GENERATING DISPLAY ELEMENTS USING SIMULATION RESULTS

(71) Applicant: Fetch, Inc., New York, NY (US)

(72) Inventors: Audrey Ruple, Blacksburg, VA (US); Johannes Paul Wowra, Darmstadt (DE); John K. Giannuzzi, Wellesley, MA (US); Danna Rabin, New York, NY (US); Christian Debes, Darmstadt (DE); Akash Gupta, Short Hills, NJ (US); Karen Leever, Westport, CT (US); Aliya McCullough, Ardmore, PA (US); Samantha McKinnon, New York, NY (US)

(73) Assignee: Fetch, Inc., New York, NY (US)

(*) Notice: Subject to any disclaimer, the term of this patent is extended or adjusted under 35 U.S.C. 154(b) by 0 days.

(21) Appl. No.: 18/362,488

(22) Filed: Jul. 31, 2023

(65) Prior Publication Data
US 2023/0376860 A1    Nov. 23, 2023

Related U.S. Application Data

(63) Continuation of application No. 18/311,517, filed on May 3, 2023, which is a continuation-in-part of application No. 17/455,268, filed on Nov. 17, 2021.

(51) Int. Cl.
*G06N 20/20*    (2019.01)
*G06N 20/00*    (2019.01)
(Continued)

(52) U.S. Cl.
CPC ............. *G06N 20/20* (2019.01); *G06N 20/00* (2019.01); *G16H 50/20* (2018.01); *G16H 50/50* (2018.01); *G16H 70/60* (2018.01)

(58) Field of Classification Search
CPC ............................... G06N 20/20; G06N 20/00
See application file for complete search history.

(56) References Cited

U.S. PATENT DOCUMENTS

| 8,489,499 B2 | 7/2013 | Yan et al. |
| D777,737 S | 1/2017 | Marshall et al. |

(Continued)

FOREIGN PATENT DOCUMENTS

| JP | 2020193989 A | 12/2020 |
| WO | 2015100236 A1 | 7/2015 |

(Continued)

OTHER PUBLICATIONS

Stott et al ("Predicted costs and benefits of eradicating BVDV from Ireland", 2012, Irish Veterinary Journal, 65:12, pp. 1-11. (Year: 2012).*

(Continued)

*Primary Examiner* — Alexey Shmatov
*Assistant Examiner* — Clint Mullinax
(74) *Attorney, Agent, or Firm* — M&B IP Analysts, LLC

(57) ABSTRACT

Techniques for predictive disease identification using simulations improved via machine learning. A method includes applying at least one machine learning model to features extracted from data including animal characteristics data of an animal, wherein outputs of the at least one machine learning model include a plurality of disease predictor values, wherein each disease predictor value corresponds to a respective disease type of a plurality of disease types, wherein each disease type of the plurality of disease types corresponds to a predetermined group of diseases; generat- (Continued)

ing disease contraction statistics based on the outputs of the at least one machine learning model; and determining, based on the disease contraction statistics, at least one disease prediction for the animal.

24 Claims, 16 Drawing Sheets

(51) Int. Cl.
  *G16H 50/20* (2018.01)
  *G16H 50/50* (2018.01)
  *G16H 70/60* (2018.01)

(56) References Cited

U.S. PATENT DOCUMENTS

| | | |
|---|---|---|
| 9,818,067 B2 | 11/2017 | Miranda et al. |
| 10,013,530 B2 | 7/2018 | Marshall et al. |
| 10,255,993 B2 | 4/2019 | Marshall et al. |
| 10,741,288 B2 | 8/2020 | Hayward |
| 10,769,729 B1 | 9/2020 | Myers et al. |
| 10,930,401 B2 | 2/2021 | Olives et al. |
| 2011/0082712 A1 | 4/2011 | Eberhardt, III et al. |
| 2013/0185097 A1* | 7/2013 | Saria ............... G06Q 10/00 705/3 |
| 2016/0316723 A1 | 11/2016 | Wall et al. |
| 2019/0026364 A1 | 1/2019 | Sankovsky |
| 2019/0333155 A1 | 10/2019 | Ramamurthy et al. |
| 2020/0202997 A1 | 6/2020 | Hadad et al. |
| 2020/0364667 A1 | 11/2020 | Marshall et al. |
| 2020/0381119 A1 | 12/2020 | Gibbs et al. |
| 2021/0012326 A1 | 1/2021 | Zelocchi |
| 2021/0117869 A1 | 4/2021 | Plumbley et al. |
| 2021/0249136 A1* | 8/2021 | Reagan ............ G06N 20/00 |
| 2021/0256615 A1 | 8/2021 | Hayward et al. |
| 2022/0391757 A1* | 12/2022 | Komori ............ G06N 3/09 |

FOREIGN PATENT DOCUMENTS

| | | |
|---|---|---|
| WO | 2021173571 A1 | 9/2021 |
| WO | 2023037317 A1 | 3/2023 |

OTHER PUBLICATIONS

Cheng et al, "Machine learning application identifies novel gene signatures from transcriptomic data of spontaneous canine hemangiosarcoma", Jul. 2021, Briefings in Bioinformatics, 22(4), pp. 1-14. (Year: 2021).*

Murphree et al., "Mac Ensemble Learning Approaches to Predicting Complications of Blood Transfusion", 2015, 2015 37th Annual International Conference of the IEEE Engineering in Medicine and Biology Society (EMBC), pp. 7222-7225. (Year: 2015).*

Murphree et al, "Mac Ensemble Learning Approaches to Predicting Complications of Blood Transfusion", 2015 37th Annual International Conference of the IEEE Engineering in Medicine and Biology Society (EMBC), pp. 7222-7225. (Year: 2015).*

Cheng et al, "Machine learning application identifies novel gene signatures from transcriptomic data of spontaneous canine hemangiosarcoma", 2021, Briefings in Bioinformatics, vol. 22, Issue 4, pp. 1-14. (Year: 2021).*

Riza Purnaramadhan. "Prediction using Monte Carlo Simulation." Mar. 26. https://medium.com/analytics-vidhya/prediction-using-monte-carlo-simulation-b006a68c284f.

* cited by examiner

TECHNIQUES FOR DISEASE PREDICTION USING MACHINE LEARNING-IMPROVED SIMULATIONS AND FOR GENERATING DISPLAY ELEMENTS USING SIMULATION RESULTS

CROSS-REFERENCE TO RELATED APPLICATIONS

This application is a continuation of U.S. patent application Ser. No. 18/311,517 filed on May 3, 2023, now pending, which is a continuation-in-part of U.S. patent application Ser. No. 17/455,268 filed on Nov. 17, 2021.

The contents of the above-references applications are hereby incorporated by reference.

TECHNICAL FIELD

The present disclosure relates generally to disease prediction using simulations which are computationally improved via machine learning, and more specifically to displaying results of such computationally improved simulations.

BACKGROUND

Predictive modeling in machine learning is the field of machine learning related to training models to output predictions. Machine learning is particularly well-suited to this task, since the lack of requirement to explicitly program the models allows for accounting for complex and varying factors. As more data becomes available, the potential for predictive models trained via machine learning becomes exponentially greater.

One particular area in which predictive modeling may be useful is for disease identification and, further, disease prediction used to provide personalized health solutions. Moreover, using machine learning to aid in learning about diseases in the realm of animals (e.g., pets such as dogs or cats) can allow for uncovering trends in animal diseases that have been yet unidentified. These uncovered trends may be very valuable for purposes such as, but not limited to, actuarial science, disease prevention, and disease mitigation.

In this regard, it is noted that more accurate disease prediction can be used to greatly improve health care for pets by providing access to information regarding potential diseases of individual pets, by altering pet care plans to avoid negative health outcomes and to overall improve pet health, and by observing broader trends in animal health outcomes.

Despite the great promise that predictive modeling via machine learning demonstrates in fields such as pet health, such modeling continues to face challenges in accurately uncovering causal relationships between combinations of animal attributes and diseases.

Additionally, when predictions are improved via machine learning, results may be displayed to users. Techniques for improving the display of those results, both in terms of retrieving information more efficiently and presenting the information represented by those results in a user-friendly manner, are therefore highly desirable.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for predictive disease identification. The method comprises: applying at least one machine learning model to features extracted from data including animal characteristics data of an animal, wherein outputs of the at least one machine learning model include a plurality of disease predictor values, wherein each disease predictor value corresponds to a respective disease type of a plurality of disease types, wherein each disease type of the plurality of disease types corresponds to a predetermined group of diseases; generating disease contraction statistics based on the outputs of the at least one machine learning model; and determining, based on the disease contraction statistics, at least one disease prediction for the animal.

Certain embodiments disclosed herein also include a system for predictive disease identification. The system comprises: a processing circuitry; and a memory, the memory containing instructions that, when executed by the processing circuitry, configure the system to: apply at least one machine learning model to features extracted from data including animal characteristics data of an animal, wherein outputs of the at least one machine learning model include a plurality of disease predictor values, wherein each disease predictor value corresponds to a respective disease type of a plurality of disease types, wherein each disease type of the plurality of disease types corresponds to a predetermined group of diseases; generate disease contraction statistics based on the outputs of the at least one machine learning model; and determine, based on the disease contraction statistics, at least one disease prediction for the animal.

Certain embodiments disclosed herein include a method for predictive disease identification. The method comprises: applying at least one machine learning model to features extracted from data including animal characteristics data of at least one animal, wherein outputs of the at least one machine learning model include a plurality of disease predictor values, wherein each disease predictor value corresponds to a respective disease type of a plurality of disease types, wherein each disease type of the plurality of disease types corresponds to a predetermined group of diseases; and generating at least one display element based on the outputs of the at least one machine learning model.

Certain embodiments disclosed herein include a method for predictive disease identification via simulations improved using machine learning. The method comprises: applying a plurality of machine learning models including a plurality of first machine learning models and a second machine learning model to features extracted from data including animal characteristics data of at least one animal, wherein the second machine learning model is a combiner model, wherein outputs of the plurality of machine learning models include a plurality of disease predictor values, wherein each disease predictor value corresponds to a respective disease type of a plurality of disease types; running a plurality of disease contraction simulations based on the plurality of disease predictor values; and generating at least one display element based on results of the plurality of disease contraction simulations.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

FIGS. 7A-J are example illustrations depicting non-limiting example visual displays of display elements created based on simulation results obtained via simulations run as described herein.

DETAILED DESCRIPTION

Figure 1:
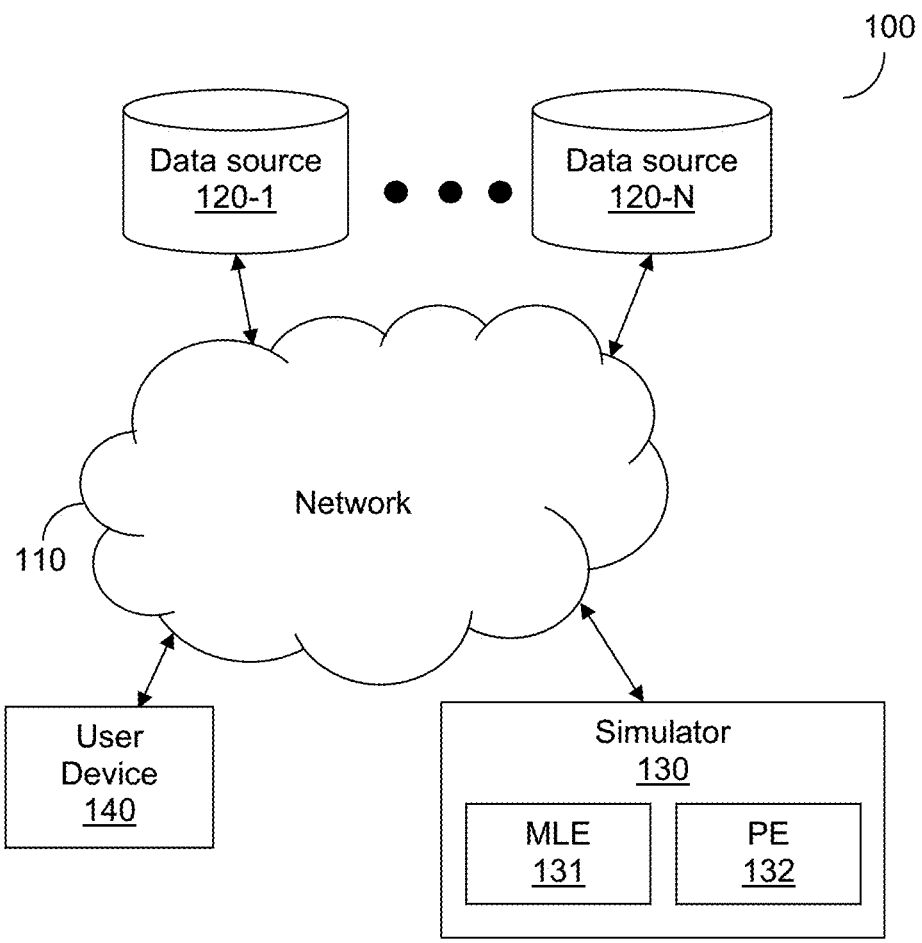
FIG. 1 is a network diagram utilized to describe various disclosed embodiments.

In light of the challenges and desired improvements noted above, techniques for improved predictive disease modeling as described herein have been developed. In particular, it has been identified that factors which influence diseases contracted by animals can be reflected in both broader categories of factors which have large sample sizes (e.g., sex, breed, common diseases, etc.) as well as narrower categories of factors with smaller sample sizes (e.g., specific ages, defined geographic locations, rare disease outcomes, etc.).

Consequently, it has been identified that performance of predictive disease modeling for animals using machine learning can be improved by utilizing both models which perform better for larger sample sizes and models which perform better for smaller sample sizes. To this end, the disclosed embodiments include a multi-stage machine learning process that uses a combiner model to combine outputs from different individual models and, in particular, individual models that have different properties and therefore perform differently for different sample sizes, in order to provide more accurate estimations of probabilities for contracting diseases and, consequently, improved disease predictions.

The disclosed embodiments further utilize the results of such predictive modeling in order to display information to users in new ways. To this end, the disclosed embodiments include various techniques for displaying insights and other information determined using the improved simulation modeling described herein. The disclosed embodiments also include techniques for improving efficiency of display element generation by storing simulation results for convenient access and retrieving stored simulation results as needed to generate display elements. The display elements may include, but are not limited to, images, graphs, insights (e.g., either textual insights or audio insights), or other portions of content projected by a device of a user in order to allow the user to observe (e.g., by sight, hearing, both, and the like) the results of the modeling represented by those display elements.

It has further been identified that there can be a need to generate predictions relative to different time periods in order to anticipate future health conditions of animals. For example, the ability to predict likelihood of contracting a given disease within 1 year, 2 years, 3 years, and the like, may allow for projecting risks of an animal developing certain conditions associated with the disease in the future. Such results may be visually presented to the user in accordance with various disclosed embodiments.

It has yet further been identified that the number of known potential diseases for animals include over 1000 distinct diseases, as well as variations which may be too numerous to individually identify. Consequently, it has been determined that predefining groups of diseases in order to group similar diseases allows for improving machine learning techniques such as techniques for classifying diseases. More specifically, limiting the number of potential outcomes to predefined groups of similar diseases instead of each distinct disease allows for striking a balance between machine learning richness with accuracy of results. Additionally, reducing the number of classes predicted reduces complexity of the model, which in turn reduces computational resources needed to apply the model. This, in turn, reduces the amount of computational resources needed to create the data based on which display elements are generated.

Similarly, the numbers of potential breeds for different kinds of animals can be enormous, with new breeds being created and bred over time. Thus, it has also been identified that predefining groups of breeds and grouping similar breeds of animals based on those predetermined groups allows for improving machine learning processes that utilize breeds as inputs. More specifically, by grouping breeds with similar genetic ancestry and using the predefined groups as inputs to a machine learning process, the machine learning process will yield overall more accurate results, particularly when breeds used as inputs include rare breeds or otherwise specific breeds which were not well-represented individually in training data.

To this end, various disclosed embodiments utilize techniques for predictive disease identification via machine learning. In an embodiment, one or more machine learning models trained to output at least disease predictor values for classifications representing different types of diseases based on at least animal characteristic features are applied to a set of animal characteristic features of an animal for which diseases are to be predicted.

Based on the output of the machine learning models, predictions indicating at least one or more diseases that the animal is likely to contract in the future are determined. The outputs of the machine learning are used to run multiple disease contraction simulations for each temporal variation of a set of multiple temporal variations. Based on those simulations, disease contraction statistics are generated. The disease contraction statistics are utilized to generate predictions about the likelihood of the animal contracting each predicted disease within different periods of time, thereby allowing for determining predictions that further indicate diseases the animal is likely to contract in different periods of time. The predictions may further be utilized to generate recommendations, insights, or both, which in turn may be used as display elements or to generate display elements as described herein.

In an embodiment, the machine learning models are applied in stages, with at least a first stage including applying an ensemble of machine learning models. The output of each model of the ensemble is input to a combiner model, which is trained to output disease predictor values for one or more diseases based on the outputs of the ensemble models. Based on the output of the combiner model, predictions indicating at least one or more diseases that the animal is likely to contract in the future are determined. In a further embodiment, determining these predictions includes running simulations based on the output of the combiner model. In another embodiment, the predictions may be determined based on the output of the combiner model without running simulations.

By utilizing the outputs of the machine learning models to run simulations of disease contraction scenarios which are also to be used for generating predictions, such simulations are run based on more accurate input parameters, thereby improving performance of the simulations themselves. This allows for generating more accurate statistics which, in turn, can be used to further improve accuracy of predictions. Moreover, applying such simulations on top of machine learning modeling allows for improving granularity of predictions as discussed above, namely, by accounting for temporal variations that allow predictions to be accurately estimated for different periods of time. Additionally, since the simulations in at least some embodiments are run based on a limited set of disease categories (i.e., a predetermined set including predefined groups of diseases), the complexity of the simulations can be reduced, which allows for running simulations more efficiently as compared to running simulations based on all potential types of individual diseases.

Further, the combined machine learning process described in accordance with various disclosed embodiments allows for increasing accuracy of disease predictions as compared to simply utilizing individual models to generate predictions, and also allow for improving accuracy of disease predictions as compared to an explicitly programmed combiner algorithm.

The result of the above is that the processes described herein demonstrate more accurate and more granular predictions than predictions made manually by veterinarians. Further, the disclosed embodiments provide an objective process for combining results of learned modeling and for predicting likelihoods of contracting diseases within different time periods which do not rely on the subjective judgments and anecdotal experience that come with manual disease prediction by such medical professionals. Consequently, the disclosed embodiments also provide more consistent results as compared to such manual techniques.

Additionally, by more accurately identifying diseases that pets are likely to have, suggestions for actions to avoid such diseases can be made more accurately. Further, the temporal variations of predictions allow for better determining relative urgencies of diseases, particularly when considering both temporal likelihoods of disease contraction and disease severity. Consequently, the disclosed embodiments may also be utilized in the clinical context in order to determine courses of action for treatment in order to prevent or mitigate disease, thereby improving animal health outcomes. Thus, the disclosed embodiments may further include applying treatments based on the insights, recommendations, or other outputs.

In addition to the various technical improvements noted herein, the improved accuracy predictions described herein can be utilized to improve pet care. In particular, visual or other displays of insights and other results of the disclosed embodiments may be utilized for educational purposes, for example by providing the information via a publicly available web portal. Such a web portal may be displayed to pet owners directly, for example, in order to allow the owners to research their own pets' health and take proactive measures to mitigate potential future conditions. Similarly, such a web portal may be displayed to a veterinarian who may utilize the insights in order to create a personalized treatment plan for a pet, or to explain some of the current and potential future conditions of pets to their owners.

Even further, individuals considering adopting pets or having pets bred may research potential conditions of different animals and breeds which, when coupled with information regarding average treatment costs for those conditions, can be utilized in order to avoid selecting pets which the potential owner cannot adequately care for (e.g., due to health and mobility, finances, environment, etc.). This, in turn, may contribute to reducing the number of pets which are bred or adopted and then abandoned, impounded, or put down. Moreover, breeds may be compared to each other in this manner, or a breed may be compared to the average for a given species of animal (e.g., based on average values for different breeds of that animal).

As a non-limiting example, a user considering adopting a dog may select a dog which is small and has a mixed breed over an Old English Mastoff, a large breed of dog which is highly prone to tearing the cruciate ligament in their hind legs. This may occur because, when presented with displayed information regarding the likelihood of injury for different kinds of dogs, the user observes that Old English Mastoff dogs have a very high probability of injury as compared to a mixed breed, smaller dog, which may be more practical given the user's finances.

FIG. 1 shows an example network diagram 100 utilized to describe the various disclosed embodiments. In the example network diagram 100, a plurality of data sources 120-1 through 120-N(hereinafter referred to individually as a database 120 and collectively as data sources 120, merely for simplicity purposes), a simulator 130, and a user device 140 communicate via a network 110. The network 110 may be, but is not limited to, a wireless, cellular or wired network, a local area network (LAN), a wide area network (WAN), a metro area network (MAN), the Internet, the worldwide web (WWW), similar networks, and any combination thereof.

The data sources 120 store data to be used for generating disease predictions and may include, but are not limited to, one or more databases (e.g., databases storing clinical data for animals), data sources available via the Internet or other networked systems, both, and the like. The data stored by the data sources 120 may include, but is not limited to, disease data, animal characteristic data, environmental data, other external factor data, combinations thereof, and the like. Such data may be in the form of textual data, visual data (e.g., images or videos), and the like.

The data sources 120 may further store outputs of the simulator 130 (e.g., recommendations, insights, display elements, etc.), display elements generated based on those outputs, both, and the like. Moreover, in accordance with various disclosed embodiments, outputs of the simulator 130 may be stored in the data sources 140 in a format which allows for more efficiently accessing and utilizing that data for generating or causing display of display elements. More specifically, in some embodiments, precalculated results determined using the simulation techniques described herein may be stored in association with respective combinations of inputs (e.g., inputs related to animal characteristics, environment, etc.) in order to allow for accessing the simulation results in order to generate statistics or otherwise to generate data to be displayed without needing to run the simulations each time such data is requested.

The disease data includes data related to diseases contracted by animals, and may further include time data indicating times at which the animals contracted certain diseases (e.g., as defined with respect to animal age). In some implementations, diseases indicated in the disease data may be grouped into predefined groups of similar diseases such that, when features are to be extracted from the disease data, specific diseases indicated by the disease data are first identified and then an applicable group of the predefined groups may be selected for each specific disease.

The animal characteristic data includes data for individual animals which may be related to disease contraction such as, but not limited to, breed, sex, age, geographic location, breed characteristics (e.g., appearance, grooming, exercise, nutrition needs, temperament, etc.), disease history, claim history (e.g., insurance claims, which may be grouped by disease type), claim costs, neutering status, pregnancy status, weight, potential symptoms of diseases (e.g., lesions, vomiting, etc.), activity tracking data (i.e., data indicating activities engaged in by animals), combinations thereof, and the like.

Breeds of the animal characteristic data may be grouped into predefined groups of similar breeds such that, when features are to be extracted from the animal characteristic data, specific breeds indicated by the animal characteristic data are first identified and then an applicable group breeds may be selected from the predefined groups of breeds for each of the identified specific breeds.

The environmental data includes data for environments in which animals live which may be related to disease contraction and may include, but is not limited to, climates of different geographic locations, relevant geographic structures (e.g., bodies of water), wildlife statistics (e.g., statistics indicating presence of other animals in the animal's environment), characteristics of a home in which an animal lives (e.g., house, apartment, etc.), combinations thereof, and the like.

The simulator 130 is configured to generate disease predictions as described herein. Such predictions are generated based on outputs of a multi-stage machine learning process that combines outputs from different models into disease predictor values for different types of diseases (e.g., specific types of diseases or groups of related diseases). To this end, the simulator 130 may include a machine learning engine (MLE) 131. The MLE 131 is configured to apply machine learning models in the multi-stage machine learning process as described herein, and may further be configured to train such models. Alternatively, another system (not shown) may be configured to train the models such that the models are trained as described herein.

The simulator 130 is further configured to determine predictions based on the outputs of the multi-stage machine learning process. To this end, the simulator 130 includes a prediction engine (PE) 132 configured to generate predictions as described herein. The predictions may further be based on simulations also described herein and, accordingly, the prediction engine 132 may be further configured to run such simulations (for example, as described below with respect to FIG. 4). In some implementations, the simulator 130 may further include a recommendation engine (not shown) configured to generate recommendations for actionable tasks to perform with respect to disease predictions for animals.

In accordance with various disclosed embodiments, the simulator 130 is also configured to generate display elements to be used for displaying results of the predictions or otherwise to be used for representing information derived from such predictions. To this end, the simulator 130 may be configured to generate charts, graphs, plots, summaries (e.g., in textual or audio form), or other content to be used as or in display elements which represent outcomes of the simulations, recommendations, or insights generated as described herein. Moreover, by generating display elements for different combinations of factors (e.g., for attributes of different breeds of animal), the display elements may be utilized to collectively demonstrate comparisons between different kinds of animals. As noted above, such comparisons may aid in selecting potential pets based on comparisons between potential challenges presented by different animals.

The user device (UD) 140 may be, but is not limited to, a personal computer, a laptop, a tablet computer, a smartphone, a wearable computing device, or any other device capable of receiving and displaying notifications. In an example implementation, the user device 140 is of a user who owns an animal as a pet. The user of the user device 140 may provide characteristics of their pet, the environment in which the pet lives, and the like, as user inputs to be used by the simulator 130 to predict diseases. The user device 140 may send these user inputs to the simulator 130, and may receive display elements to be displayed representing disease predictions, recommendations, insights, or combinations thereof, from the simulator 130.

Figure 2:
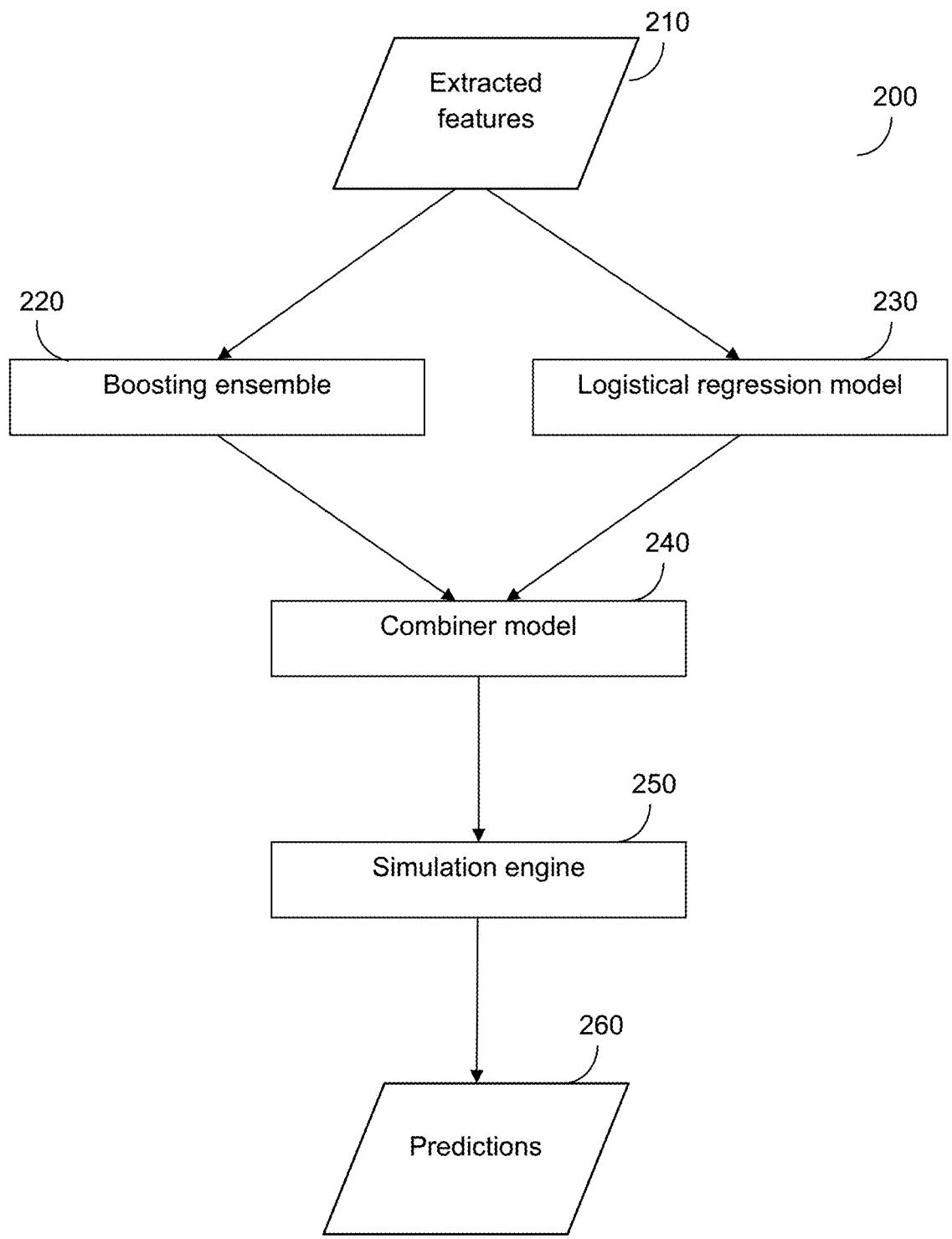
FIG. 2 is a flow diagram illustrating a multi-stage machine learning approach to predictive disease identification according to an embodiment.

FIG. 2 is a flow diagram 200 illustrating a multi-stage machine learning approach to predictive disease identification according to an embodiment.

In an embodiment, features 210 extracted from data related to an animal are input to a first stage of machine learning models. In the embodiment depicted in FIG. 2, the first stage of machine learning models includes a boosting ensemble 220 and a logistic regression model 230 such that the features 210 are input to both the boosting ensemble 220 and to the logistic regression model 230.

The boosting ensemble 220 is an ensemble of sequentially applied boosting machine learning models (models of such a boosting ensemble being referred to herein as boosting machine learning models, not depicted in FIG. 2) trained using a boosting algorithm. Such a boosting algorithm sequentially trains models of the ensemble, where misclassifications by a model in the sequence made during training are used to adjust weights of subsequent models in the sequence. A boosting algorithm operates based on the principle of combining predictions of multiple weak learner models in order to form one strong rule for making predictions. In an embodiment, the output of the boosting ensemble is a disease predictor value (e.g., a probability) for each potential outcome, where each potential outcome is a disease type (e.g., a particular disease or a predefined group of diseases). It is noted that boosting ensembles tend to make predictions more accurately when applied to data from large sample sizes.

The logistic regression model 230 is a machine learning model trained to output a dependent variable with a finite number of potential outcomes. As a non-limiting example, a binary regression model outputs either A or B. As another non-limiting example, a multinomial regression model outputs one of a set such as A, B, C, or D. In an embodiment, the output of the logistic regression model is a disease predictor value (e.g., a probability) for each potential outcome, where each potential outcome is a disease type (e.g., a particular disease or a predefined group of diseases). It is noted that logistic regression models tend to make predictions more accurately when applied to small sample sizes.

In an embodiment, each of the boosting ensemble 220 and the logistic regression model 230 is trained to output a disease predictor value for each potential outcome (e.g., each type of disease which may be contracted by an animal), where the potential outcomes for both the boosting ensemble and the logistic regression model are the same set of potential outcomes. As a non-limiting example, when the potential outcomes include 70 distinct predefined groups of diseases representing 70 different disease types, each of the boosting ensemble and the logistic regression model may be trained to output a probability for each of the 70 predefined groups of diseases.

It should be noted that, at least in some embodiments, other types of machine learning models may be utilized during the first stage of machine leaning model application, either in addition to or instead of either the boosting ensemble 220 or the logistic regression model 230. In particular, other models which tend to demonstrate high accuracy for larger sample sizes may be utilized in addition to or instead of the boosting ensemble 220, and other models which tend to demonstrate high accuracy for smaller sample sizes may be utilized in addition to or instead of the logistic regression model 230.

The combiner model 240 is trained to utilize outputs of the first stage machine learning models 220 and 230 and in order to output a disease predictor value for each potential outcome, where each potential outcome is a disease type (e.g., a particular disease or a predefined group of diseases).

Given the above properties of boosting ensembles and logistic regression models, in an embodiment, the combiner model is trained to utilize outputs from a boosting ensemble with outputs from a logistic regression model in order to output a single set of disease predictor values. The result of this combination is a combiner model which accounts for variations due to both large and small sample sizes in order to more accurately predict diseases. In this regard, it has been identified that the combination of a boosting ensemble and a logistic regression model yields particularly accurate results in the context of disease prediction for pets and other non-human animals.

The outputs of the combiner model 240 are provided to a simulation engine 250 configured to determine predictions 260 of disease for animals. In a further embodiment, the simulation engine 250 may be further configured to output risk scores for a given animal contracting certain types of diseases (e.g., risk scores determined based on the probability of contracting each disease type), and to include those risk scores with the predictions 260.

Figure 4:
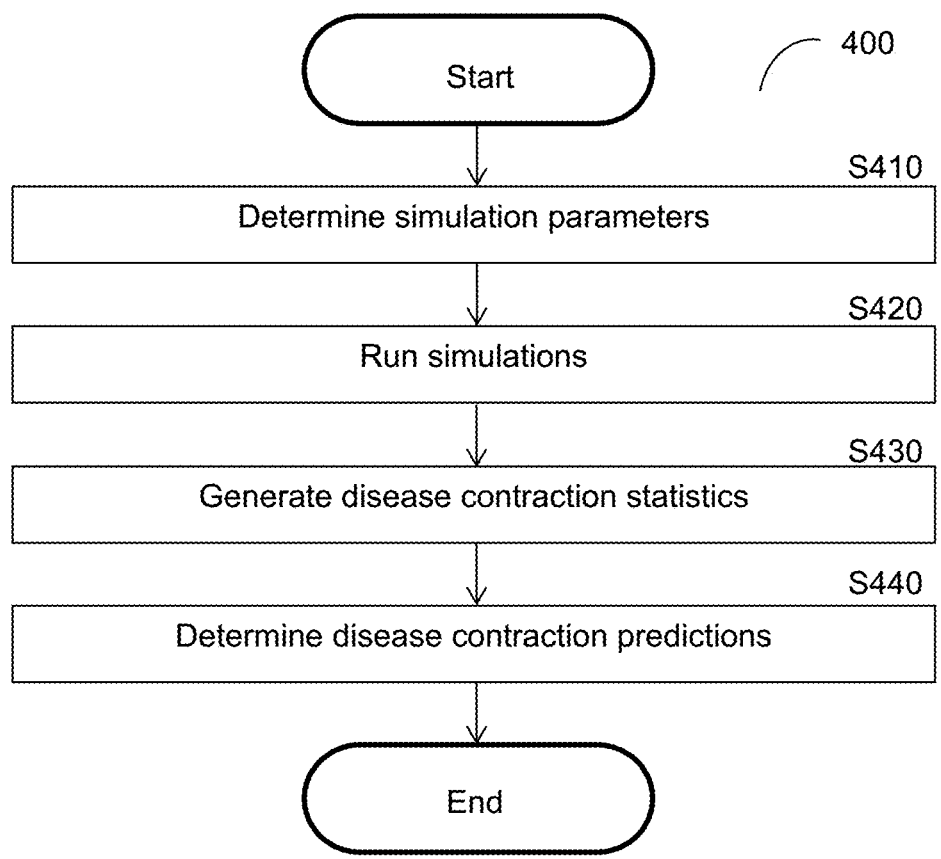
FIG. 4 is a flowchart illustrating a method for determining a predictions for different temporal ranges according to an embodiment.

In various embodiments, the simulation engine 250 may be further configured to perform simulations in order to determine temporal variations of disease prediction as described further herein, for example, as described with respect to FIG. 4.

Figure 3:
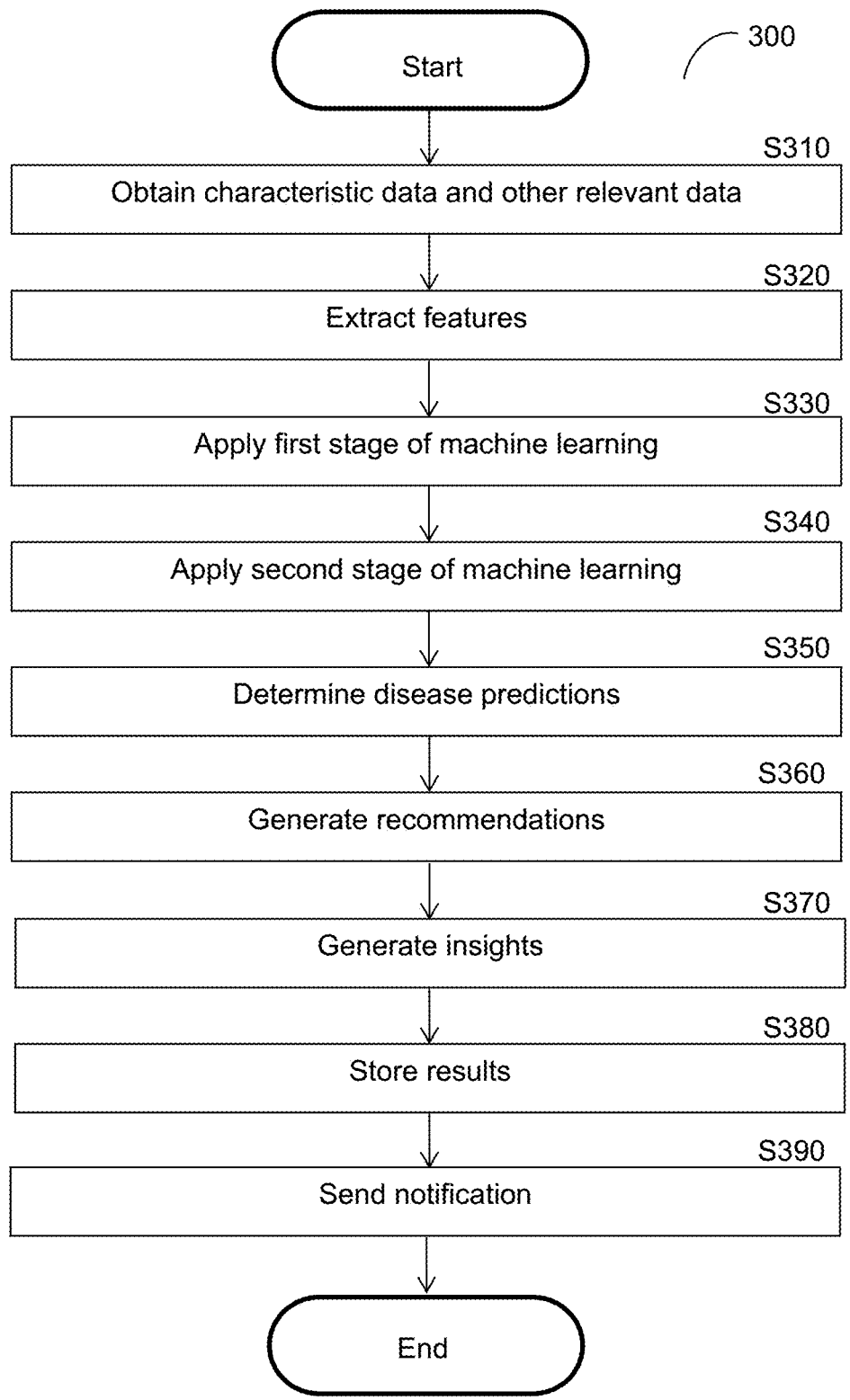
FIG. 3 is a flowchart illustrating a multi-stage machine learning method for predictive disease identification according to an embodiment.

FIG. 3 is a flowchart 300 illustrating a multi-stage machine learning method for predictive disease identification according to an embodiment. In an embodiment, the method is performed by the simulator 130, FIG. 1.

At S310, animal characteristic data and other data to be used for determining disease predictions for an animal are obtained. The data may be received (e.g., from a user device such as the user device 140, FIG. 1) or may be retrieved (e.g., from a data source such as one of the data sources 120, FIG. 1). When the data is retrieved, such retrieval may be based on an identifier of the animal for which predictions are to be determined.

At S320, features to be used as inputs to the first stage of machine learning are extracted from the data obtained at S310.

In an embodiment, S320 may further include enriching the data obtained at S310 in order to provide more features to be used for the first stage of machine learning. Enriching the data may include, but is not limited to, retrieving relevant data based on other obtained data, inferring new data based on the obtained data, both, and the like. As non-limiting examples, climate data may be retrieved based on geographic locations indicated in the obtained data (i.e., climate data for those geographic locations is retrieved), neutering status or other medical records may be retrieved based on an identifier of an animal, claim history and costs may be retrieved based on an identifier of an animal, and the like.

In embodiments where enriched data is at least partially inferred, such inferences may be derived using machine learning. To this end, S320 may include applying a machine learning model trained to infer enrichment data using historical data and historical enrichment data. As a non-limiting example, such a model may be trained to output a classification of sex (e.g., male or female) based on inputs including (but not necessarily limited to) animal name.

At S330, a first stage of machine learning is conducted using the extracted features. The first stage of machine learning includes applying multiple machine learning models of different types. Each model or combination of models (e.g., an ensemble including a subset of models) among the multiple machine learning models ultimately outputs a respective first disease predictor value for each potential disease type (e.g., potential classifications of the models) to be input to a combiner model as described below with respect to S340.

In an embodiment, the first stage of machine learning includes applying a boosting ensemble, a logistic regression model, or both, to the extracted features or a portion thereof. The types of models applied during the first stage of machine learning are different such that, for example, when a boosting ensemble is applied during the first stage of machine learning, at least one non-boosting model is also applied during the first stage of machine learning and, when a logistic regression model is applied, at least one non-logistic regression model is also applied. As noted above, boosting ensembles and logistic regression models perform differently with different sample sizes of data such that using both types of models allows for more accurate outputs when applied to datasets of varying sample sizes such as datasets related to animal characteristics (i.e., since some animal characteristics are more common than others and therefore are demonstrated in larger sample sizes).

In a further embodiment, any or all of the machine learning models applied during the first stage of machine learning are supervised learning models trained to output disease predictor values for certain disease types in which the training of those supervised learning models uses a labeled training set. Such a labeled training set includes training input data (e.g., data indicating animal characteristics, environmental factors, etc.) as well as predefined training labels representing the "correct" outputs for respective combinations of training input data.

At S340, a second stage of machine learning is conducted using the outputs of the first stage of machine learning models. In an embodiment, the second stage of machine learning includes applying a combiner model to the outputs from the machine learning models of the first stage of machine learning. The combiner model is trained to combine outputs from the first stage of machine learning models in order to output a second disease predictor value for each potential disease type. To this end, the combiner model includes respective weights for the different models or ensembles utilized in the first stage of machine learning. Like the models applied during the first stage of machine learning, the combiner model may be trained via a supervised machine learning process using labeled training data including output training labels indicating disease predictions associated with different combinations of training inputs.

At S350, one or more disease predictions are determined for the animal based on the output of the second stage of machine learning. In an embodiment, each disease prediction may indicate a disease type (e.g., a specific disease or a predefined group of diseases) that the animal is likely to contract.

Alternatively or collectively, the disease predictions may indicate the likelihood of contracting certain diseases (e.g., as defined with respect to the disease predictor values output by the combiner model). In a further embodiment, an animal is likely to contract a disease when the disease predictor value for that disease output by the combiner model during the second stage of machine learning is above a predetermined threshold. As a non-limiting example where the disease predictor value is a probability, an animal may be determined to be likely to contract a disease when the probability of contracting the disease is above 60% (i.e., 0.6). To this end, in some embodiments, S350 may further include generating risk scores for each disease type based on the disease predictor values output by the combiner model.

Each risk score may indicate, for example, a degree of risk of the animal contracting the disease type (e.g., a risk score in the range of 1 to 10, with 1 being low risk and 10 being high risk). The risk scores may include risk scores indicating likelihood of the animal contracting a disease within its lifetime (e.g., based on an average lifespan of animals having the same or similar characteristics), risk scores indicating likelihood of the animal contracting a disease within a certain time period (e.g., within 3 years from now, at a certain stage of development, etc.), both, and the like.

In another embodiment, determining the disease predictions may further include running simulations for the animal based on the disease predictor values output at S340. In a further embodiment, the simulations may be performed with respect to different periods of time such that the results of the simulations may be utilized to determine disease predictions for the same animal with respect to those different time periods. This, in turn, allows for providing increased granularity disease predictions.

An example method for determining disease contraction predictions and, in particular, disease contraction predictions with respect to different time periods, using simulations is now described with respect to FIG. 4. FIG. 4 is a flowchart 400 illustrating a method for determining predictions for different temporal ranges according to an embodiment.

At S410, simulation parameters are determined. The simulation parameters define how the simulations are run and may be determined at least partially based on probabilities or other disease predictor values indicating the likelihood of an animal contracting certain diseases in combination with predetermined rules for determining simulation parameters using those disease predictor values. The simulation parameters include time periods for which simulations are to be run (e.g., within 1 year from present, within 2½ years from present, between 2 years and 3 years from present, etc.). As another example, the time periods may correspond to different stages in an animal's development such as, but not limited to, baby, young, mature, and geriatric, with each stage corresponding to a time period in an animal's life.

In an example implementation, the simulations may be Monte Carlo simulations. To this end, in some embodiments, S420 may further include assigning multiple values to variables used for the simulations based on disease predictor values for contracting different diseases (e.g., probabilities output by the combiner model as described above with respect to S340).

Monte Carlo simulations predict a set of outcomes based on an estimated range of values versus a set of fixed input values. For any variables with uncertain values, a model of possible results is created by utilizing a probability distribution to identify such potential results. Then, a Monte Carlo experiment can be run by running many simulations to produce a large number of likely outcomes. To this end, in an embodiment, S420 may further include determining a probability distribution for each potential disease type based on a disease predictor value corresponding to the disease type (e.g., probabilities output by the combiner model as described above with respect to S340) and creating a model of possible results for each disease type using the respective probability distribution for that disease type.

At S420, disease contraction simulations are run using the determined simulation parameters. In an embodiment, S420 includes running at least a predetermined number of simulations (e.g., 1,000 simulations) such that a large number of likely outcomes may be determined.

In this regard, it is noted that Monte Carlo simulations can be effectively leveraged for long-term predictions since such simulations exhibit increased accuracy for outcomes (even outcomes with projections that are farther out in time) as the number of inputs increase. Thus, Monte Carlo simulations provide the ability to accurately predict outcomes over time such that it has been identified that Monte Carlo simulations can be utilized to provide accurate temporal forecasting in accordance with the disclosed embodiments.

At S430, disease contraction statistics are generated based on the outcomes of the disease contraction simulations. The disease contraction statistics may include, but are not limited to, mean, standard deviation, both, and the like. Moreover, the disease contraction statistics are defined with respect to different time periods such that the statistics can be utilized to predict likelihood of contracting diseases in the different time periods.

At S440, predictions of disease contraction are generated for the animal based on the disease contraction statistics. As a non-limiting example, the likelihood that the animal contracts a given disease during a given time period may be determined at least based on the average time until animals of the same species and breed develop that disease.

Returning to FIG. 3, at optional S360, one or more recommendations are generated based on the determined disease predictions. Each recommendation may be, but is not limited to, an individualized recommendation for improving pet health and/or avoiding undesirable health outcomes such as contracting certain diseases or mitigating the severity of diseases the animal is likely to contract. To this end, the recommendations may include actions to be taken with respect to the animal such as, but not limited to, losing weight, changes in diet, and the like.

Moreover, in some embodiments, the recommendations include suggestions related to how a user should care for an animal or whether a user should assume care for an animal (e.g., by adopting or breeding the animal) based on one or more inputs related to the user's ability to care for the animal. To this end, in such embodiments, S360 may include applying one or more care assumption recommendation rules defined with respect to potential disease predictions and user inputs. Such rules may, for example, result in personalized recommendations to be used when caring for pets in order to improve their pets' health long term. Such recommendations may be provided, for example, to a device operated by a pet owner or by a veterinarian for use in determining personalized care plans for pet owners.

Another potential use may be to provide recommendations for assuming care for animals only when the disease prediction forecasted for the animal indicates that the animal is unlikely (e.g., likelihood below a threshold) to develop diseases known to have predetermined required treatments or care where the user inputs indicate that the user has one or more predetermined status markers (e.g., status markers defined with respect to health, mobility, finances, residence, etc.) which are incompatible with the required treatments or care. As a non-limiting example, such a rule may be defined such that a recommendation not to adopt a 4-year-old English Bulldog (a dog belonging to a Mastiff-like breed) is generated when user inputs indicate that a user cannot afford care expenses in excess of $3,000 during the next 5 years.

At optional S370, one or more insights may be generated based on disease predictions for multiple animals. The insights may include, but are not limited to, likelihoods of developing different diseases over one or more periods of time or stages in an animal's lifetime, insights regarding care of animals, average or otherwise expected costs of health treatments for animals developing the predicted diseases, combinations thereof, and the like. The insights may be insights related to general factors such as breed, may be determined for combinations of factors (e.g., animals having in common some combination of the same breed, sex, weight range, age or age range, geographic location such as Zone Improvement Plan [ZIP] code, etc.), both, and the like.

In various embodiments, the insights may further include insights related to accidents, for example, likelihood of an animal having an accident represented as accident risk values. Such insights may be derived based on the disease predictions. More specifically, certain diseases or certain known conditions associated with certain diseases may correlate to a higher risk of accident, which could have effects on the animal's health. To this end, in some embodiments, S370 may further include determining such accident risk values based on disease predictions, environmental factors, trends, combinations thereof, and the like.

In a further embodiment, the insights may include one or more disease risk scores, one or more accident risk scores, or both. Each such score represents a likelihood that an animal develops an issue (e.g., a particular disease or one of a group of diseases for disease risk score, or having an accident for accident risk score). These scores may be determined based on simulation results. As a non-limiting example, simulations may yield a certain number of dogs developing a disease among the disease group "oral inflammation" out of a total population of dogs, and the percentage of dogs which develop one of those diseases as compared to the entire population may be used to determine a disease risk score for that disease.

In an embodiment, S370 includes comparing between the disease predictions for multiple animals to actual results (i.e., historical diseases actually contracted by those animals). To this end, in such embodiments, steps S310 through S350 may be repeated for multiple iterations (each iteration providing predictions for a respective animal based on input data related to that animal), and the analysis at S370 is based on the aggregated results of those iterations. Moreover, the iterations may utilize animals with similar characteristics (e.g., same species, same sex, same or related breed, same weight, similar environment, combinations thereof, etc.) such that trends can be based on like comparisons.

By comparing between predicted results and actual results, trends representing changes in disease contraction can be identified, which in turn allows for generating insights that demonstrate broader trends reflected in aggregated differences between what would normally be expected and what actually occurred. To this end, in some embodiments, S370 includes comparing results of simulations (e.g., the simulations run as described with respect to FIG. 4) run with respect to certain time periods to actual results for those time periods.

By comparing predicted results to actual results for a time period in which certain events occur, trends which may correlate with or be caused by that event can be unearthed. As a non-limiting example, by comparing predicted results for the time period between March 2020 and March 2021 which represents the first year of the novel Coronavirus pandemic to actual results for that same time period, trends in animal health which may be related to the pandemic may be identified. Such trends may include, for example, increases in insurance claims compared to expected claims during the time period in question, decreases in certain behavioral diseases during the time period in question, combinations thereof, and the like.

At S380, results of at least some of the above steps are stored for subsequent use. In an embodiment, the disease contraction statistics, predictions of disease contraction, recommendations, insights, or a combination thereof, may be stored.

In a further embodiment, such results may be stored in a lookup table, indexed according to animal characteristics or combinations of factors including animal characteristics. The animal characteristics or combinations of factors may be used for subsequent lookup, for example, when a user provides a certain combination of factors as user inputs for a particular animal or kind of animal, the relevant disease contraction statistics, predictions, recommendations, insights, or combination thereof, may be retrieved from the lookup table. In yet a further embodiment, display elements may be stored in association with factors or combinations of factors in addition to or instead of the results themselves.

As a non-limiting example, each set of results may be stored in association with a respective set of values for four factors: breed, age, sex, and ZIP code. Thus, results for a Corgi dog, age 3 years old, female, and ZIP code 01234 may be stored with those values, and whenever a user provides "Corgi", "3", "female", and "01234" as inputs as part of a request, the results corresponding to that set of values can be retrieved.

Moreover, such a lookup table may include lookup results which are generic to any animal having certain characteristics (e.g., corgi, age 3, female, ZIP code 01234), may include lookup results which are specific to particular animals having certain medical histories (e.g., one such set of results may be stored for the corgi called "Maxine" who is age 3, female, lives at ZIP code 01234, and has a history of diseases in the family vomiting and diarrhea).

Storing the results of prior simulations in such a lookup table allows for reducing use of computing resources when display elements are to be generated based on those results. More specifically, results of prior simulations (e.g., the direct results, predictions, recommendations, or insights determined based on prior simulations) may be stored such that the simulations do not need to be run again each time that display elements are to be generated based on those simulations. Additionally, lookups can be performed faster than full simulations, thereby saving time. Storing the display elements themselves further reduces processing needed for generating display results, particularly when displays are requested by many users in a short period of time. These benefits provide even further benefits when storing lookup results which are personalized to individual animals, as those personalized simulation results cannot be extrapolated based on generic characteristics alone.

At optional S390, a notification may be sent. The notification may indicate, but is not limited to, the disease predictions, the recommendations, the insights, a combination thereof, and the like. The notification may be sent to a user device (e.g., the user device 140, FIG. 1), for example, a user device of a user who owns a particular animal as a pet or a user device of an administrator or other person who wishes to receive insights related to broader trends among animals.

It should be noted that the steps of FIG. 3 are depicted in a specific order for example purposes, but that the steps of FIG. 3 are not necessarily limited to the order depicted therein. In particular, steps S360 and S370 may be performed in any order or in parallel without departing from the scope of the disclosure.

Additionally, it should also be noted that FIG. 3 depicts a single iteration of disease prediction merely for simplicity purposes, and that multiple iterations of disease predictions may be performed without departing from the disclosed embodiments. These iterations may be performed sequentially (e.g., multiple disease predictions for the same animal or for different animals), in parallel (e.g., disease predictions for multiple different animals), both, and the like.

Sequentially performing iterations allows for, among other things, updating disease predictions, for example as new data about the animal becomes available. As a non-limiting example, whenever a disease prediction is required (for example, when a new insurance claim is submitted), a new disease prediction may be made based on the current data for the animal to ensure that the new disease prediction is based on up-to-date data. As another non-limiting example, new disease predictions may be determined through subsequent iterations when new data about the animal becomes available or otherwise when the animal characteristics or other data related to the animal is updated. Such changes may include, but are not limited to, updates to the animal's location (e.g., when the animal's owner moves), when a previously unknown sex of the animal has been determined, when the animal has been spayed or neutered, when a breed of the animal is updated, combinations thereof, and the like.

Figure 5:
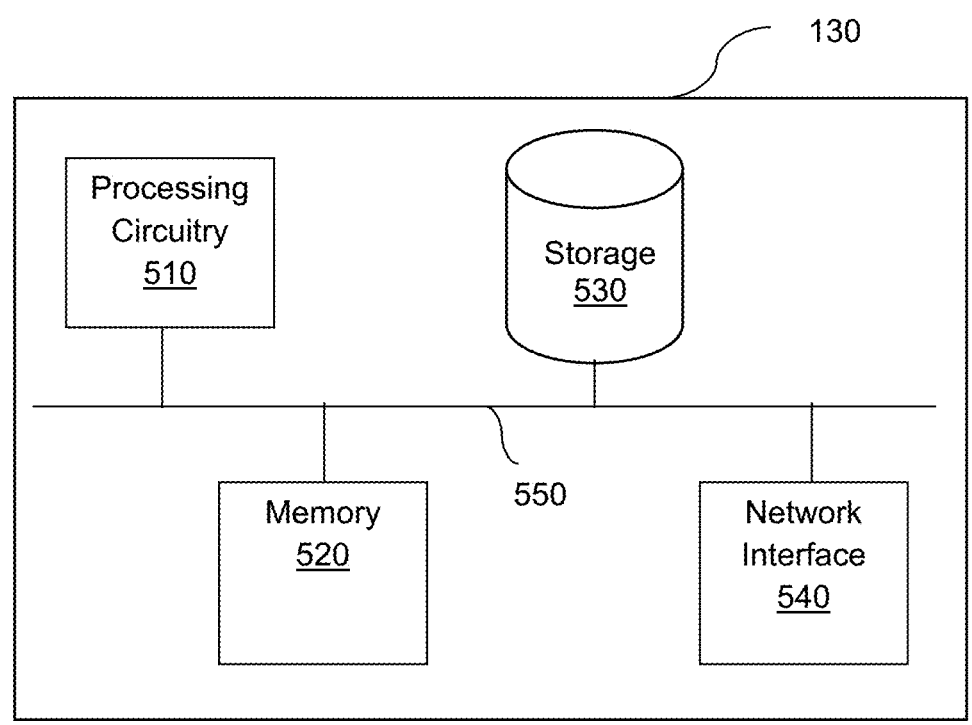
FIG. 5 is a schematic diagram of a disease predictor according to an embodiment.

FIG. 5 is an example schematic diagram of a simulator 130 according to an embodiment. The simulator 130 includes a processing circuitry 510 coupled to a memory 520, a storage 530, and a network interface 540. In an embodiment, the components of the simulator 130 may be communicatively connected via a bus 550.

The processing circuitry 510 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 520 may be volatile (e.g., random access memory, etc.), non-volatile (e.g., read only memory, flash memory, etc.), or a combination thereof.

In one configuration, software for implementing one or more embodiments disclosed herein may be stored in the storage 530. In another configuration, the memory 520 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 510, cause the processing circuitry 510 to perform the various processes described herein.

The storage 530 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The network interface 540 allows the simulator 130 to communicate with, for example, the agent 140.

It should be understood that the embodiments described herein are not limited to the specific architecture illustrated in FIG. 5, and other architectures may be equally used without departing from the scope of the disclosed embodiments.

Figure 6:
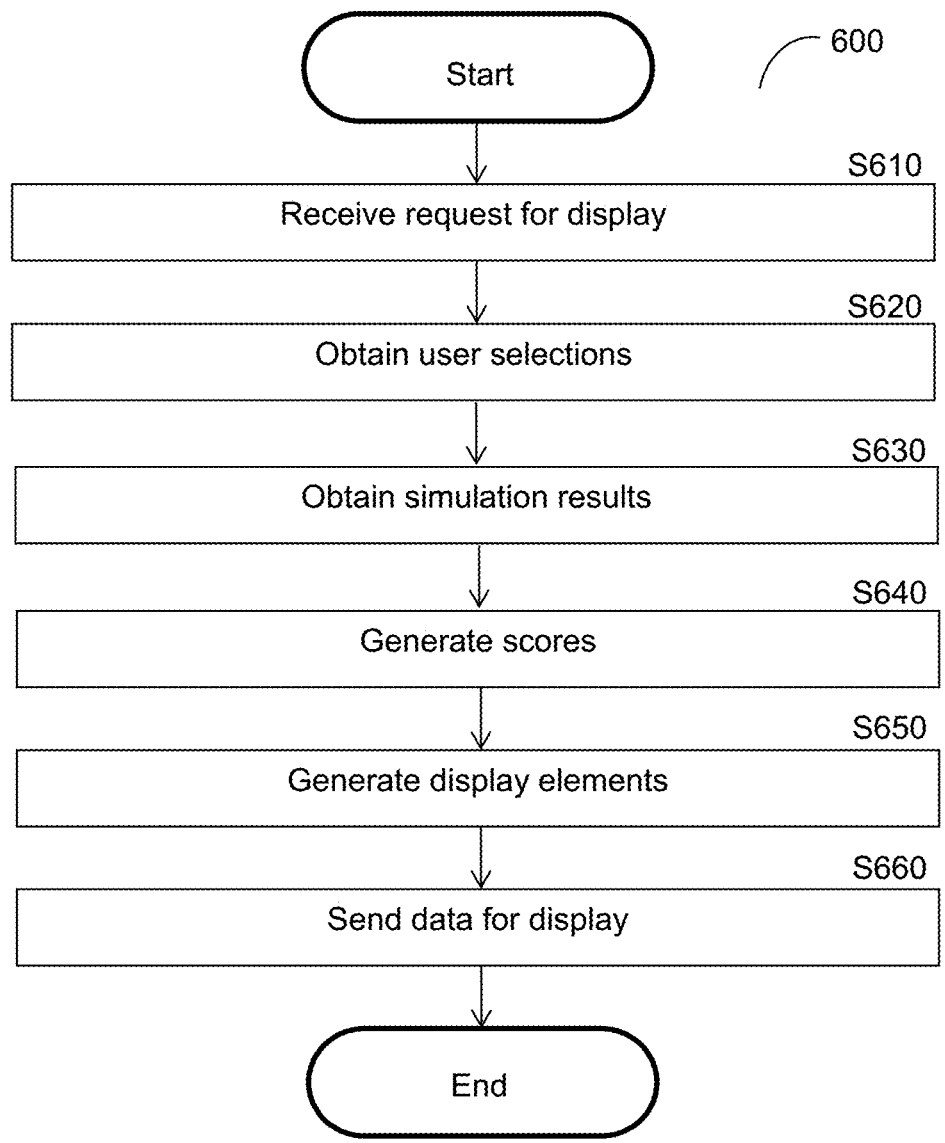
FIG. 6 is a flowchart illustrating a method for displaying simulation results according to an embodiment.

FIG. 6 is a flowchart 600 illustrating a method for displaying simulation results according to an embodiment. In an embodiment, the method is performed by the simulator 130, FIG. 1

At S610, a request for display is received. The request may include one or more user inputs such as, but not limited to, inputs indicating animal attributes, environmental attributes, information about the user, combinations thereof, and the like. The request may be received, for example, in response to interactions by a user (e.g., a user of the user device 140, FIG. 1), and in particular in response to interactions through which the user provides one or more user inputs to be used for identifying applicable simulation results.

At S620, one or more user selections are identified. The user selections may be identified based on selections previously made by a user (e.g., a user interacting with a GUI) and may include, but are not limited to, animal attributes such as breed. As a non-limiting example, a user may select a breed from among a library of potential breeds and/or breed groups, and such a selection may be identified as a breed or group of breeds for which simulation results are to be obtained.

At S630, simulation results are obtained. The simulation results may be obtained by performing simulations as described in any of the embodiments discussed above, or may be retrieved (e.g., from a lookup table). In an embodiment, the simulation results are based on simulation outputs generated as discussed above with respect to FIGS. 2 through 4. Also as noted above, the simulation results may be stored (e.g., in a lookup table) and retrieved at S630 when displays are requested in order to allow for producing displays based on those simulation results more efficiently and quickly as compared to running the simulations each time such a request is received.

At S640, one or more insights are determined based on the obtained simulation results. In an embodiment, the insights are generated as described above with respect to S370. To this end, S640 may include generating such insights or identifying previously stored insights (e.g., insights stored as part of the simulation results obtained at S630, for example simulation results stored as discussed above with respect to S380).

At S650, one or more display elements are generated. The display elements may be or may include, but are not limited to, graphical user interface (GUI) elements including charts, graphs, text, or other representations of data determined directly or indirectly based on simulation results.

At S660, data is sent for display. The data may include, but is not limited to, the generated display elements, and may be sent to a user device (e.g., the user device 140, FIG. 1).

FIGS. 7A through 7J are example illustrations 700A through 700K, respectively, depicting non-limiting example visual displays of display elements created using simulations run as described herein. The various illustrations 700A through 700K show potential graphical user interfaces (GUIs) populated with display elements generated based on simulation results. These views may be presented, as a non-limiting example, as part of a web portal available via the Internet.

Figure 7A:
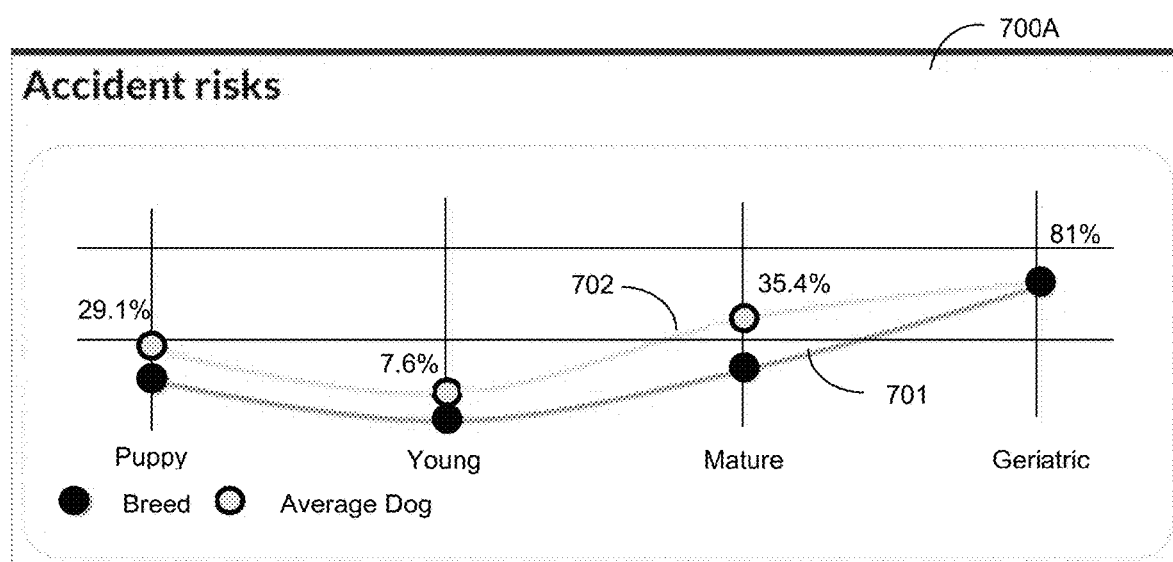

FIG. 7A depicts an illustration 700A of two plots 701 and 702 of a set of plots demonstrating a likelihood of accident ("accident risk") for dogs at different stages in development ("puppy", "young", "mature", and "geriatric"). The plot 701 depicts likelihoods of accidents at each of these stages for a particular breed of dog, while the plot 702 depicts likelihoods of accidents for the average dog across breeds (e.g., an average of the likelihood of accidents for each breed of dog determined based on outcomes of simulations). In the non-limiting example shown in FIG. 7A, the plots 701 and 702 demonstrate that this breed of dog is at lower risk of accident than the average dog at most stages of development. The graph including these plots may be a display element generated based on simulation results as described herein.

Figure 7B:
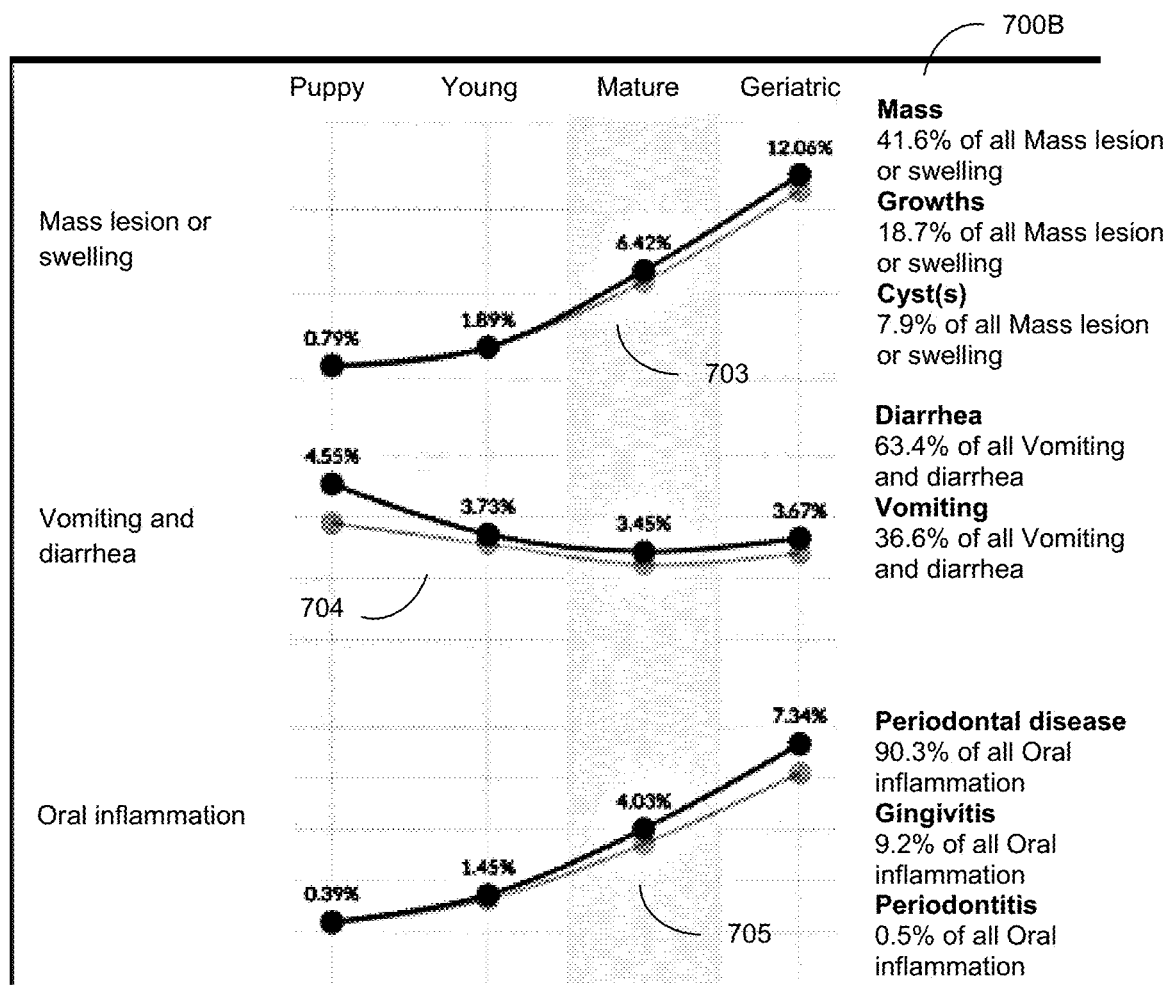

FIG. 7B depicts an illustration 700B of three sets of plots 703, 704, and 705. As illustrated in FIG. 7B, each set of plots 703, 704, and 705 is a pair of plots demonstrating probabilities for a respective condition which may be related to a disease determined based on outcomes of simulations. More specifically, the plot 703 shows likelihood of a dog developing mass lesions or swelling at different stages in development, the plot 704 shows likelihood of a dog developing recurring issues with vomiting and diarrhea at different stages in development, and the plot 705 shows likelihood of a dog developing oral inflammation at different stages in development.

Moreover, as illustrated in FIG. 7B, each of the sets of plots 703, 704, and 705 is accompanied by a more detailed breakdown of different disease groups. For example, under the disease group "Mass lesion or swelling", a breakdown shows percentages indicating, on average, how much of dogs developing "Mass lesion or swelling" demonstrate mass, growths, and cysts, respectively. Likewise, for the disease group "Vomiting and diarrhea", a breakdown shows percentages indicating, on average, how much of dogs developing "Vomiting and diarrhea" demonstrate diarrhea and vomiting, respectively. For the disease group "Oral inflammation", a breakdown shows percentages indicating, on average, how much of dogs developing "Oral inflammation" demonstrate periodontal disease, gingivitis, and periodontitis, respectively. The graphs showing these plots may form a display element generated based on simulation results as described herein.

Figure 7C:
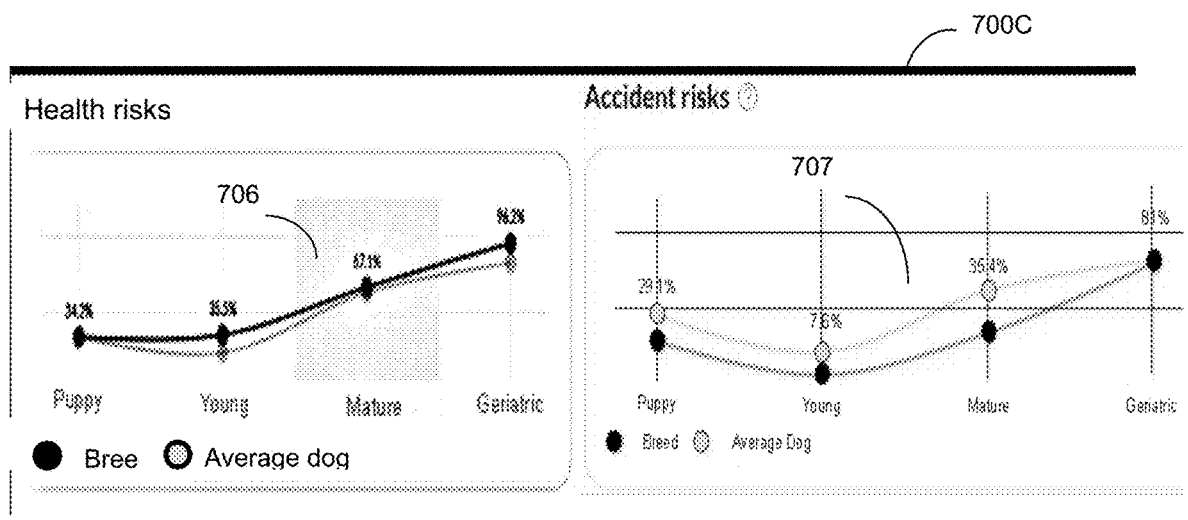

FIG. 7C depicts an illustration 700C of two sets of plots 706 and 707 demonstrating health risks and accident risks, respectively. Each of the sets of plots 706 and 707 has a plot representing average risk of developing a health condition or having an accident, respectively, at different stages in development for a dog having particular attributes; and a plot representing average risk of developing a health issue or having an accident, respectively, at different stages in development for the average dog. The graph including each set of plots 706 and 707 may be a display element generated based on simulation results as described herein.

Further, as shown in FIG. 7C, additional display elements in the form of graphical user interface (GUI) fields 708, 709, and 710 are included alongside the sets of plots 706 and 707. The field 708 represents an age of a dog, the field 709 represents a ZIP code (e.g., a ZIP code of a user caring for or considering adopting the dog), and the field 710 represents a sex of the dog. A user may interact with the fields 708, 709, and 710 via a GUI in order to provide values as user inputs, and simulation results may be determined by either running simulations using those user inputs or by looking up that combination of user inputs in a lookup table (not shown). In the non-limiting example shown in FIG. 7C, the specific kind of dog (i.e., not the average dog) represented in one of the plots of each of the sets of plots 706 and 707 may be a dog having a combination of attributes including a specific breed, an age of 7, a ZIP Code of 24060, and a sex of male.

Figure 7D:
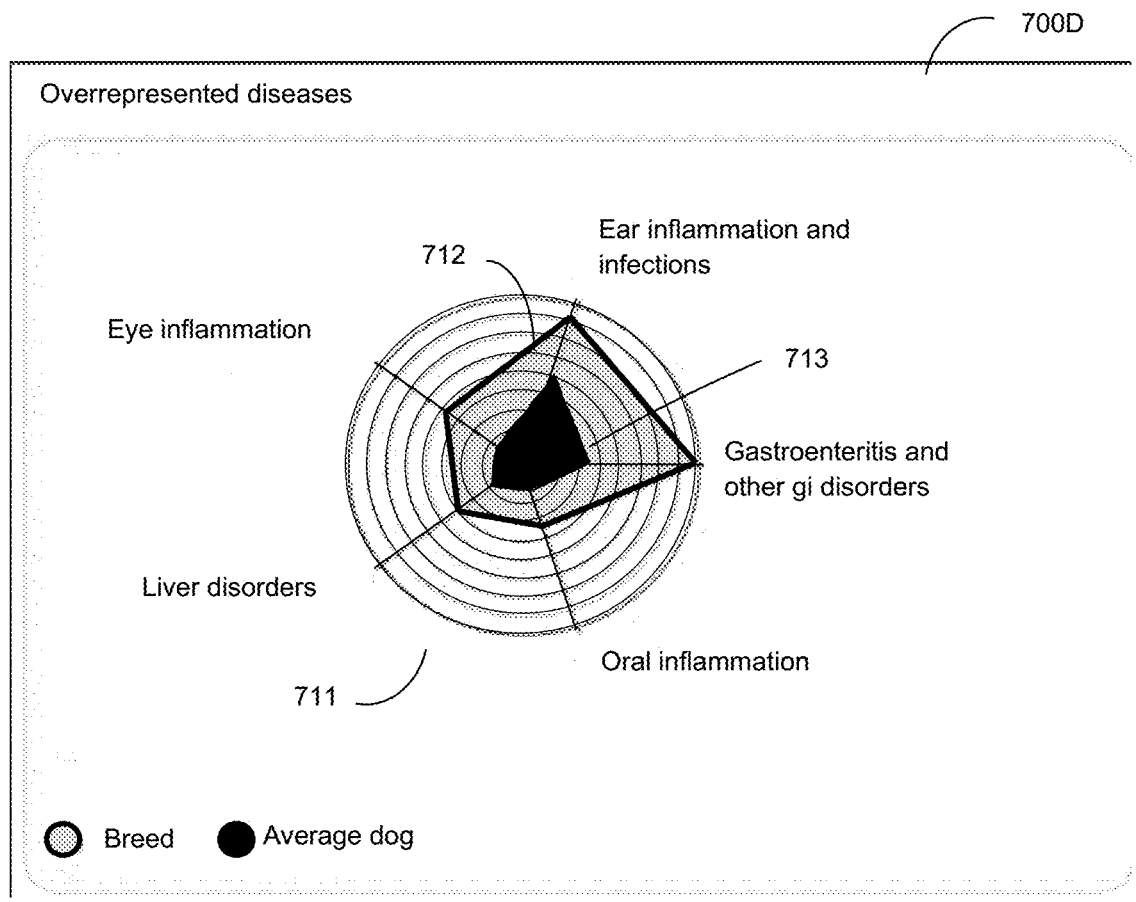

FIG. 7D depicts an illustration 700D of a display element including a spider chart or radar chart 711. The radar chart 711 includes a first plot 712 and a second plot 713. The first plot 712 demonstrates a proclivity for developing certain kinds of overrepresented diseases for dogs of a specific breed, and the second plot 713 demonstrates a proclivity for developing those kinds of diseases for the average dog.

Figure 7E:
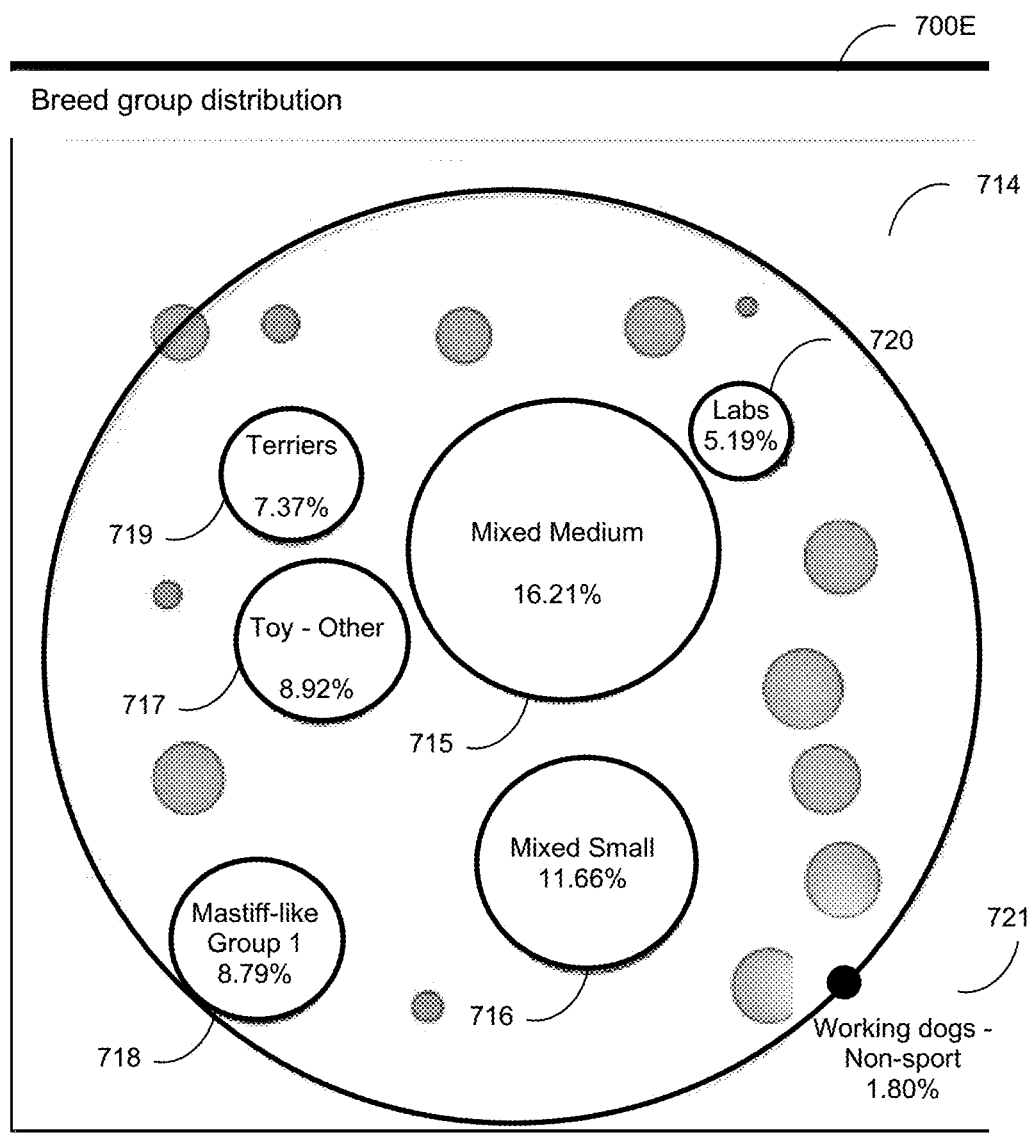

FIG. 7E depicts an illustration 700E of a display element including a bubble chart 714. The bubble chart 714 includes multiple bubbles 715 through 721, where each of the bubbles 715 through 721 representing respective groups of breeds.

Figure 7F:
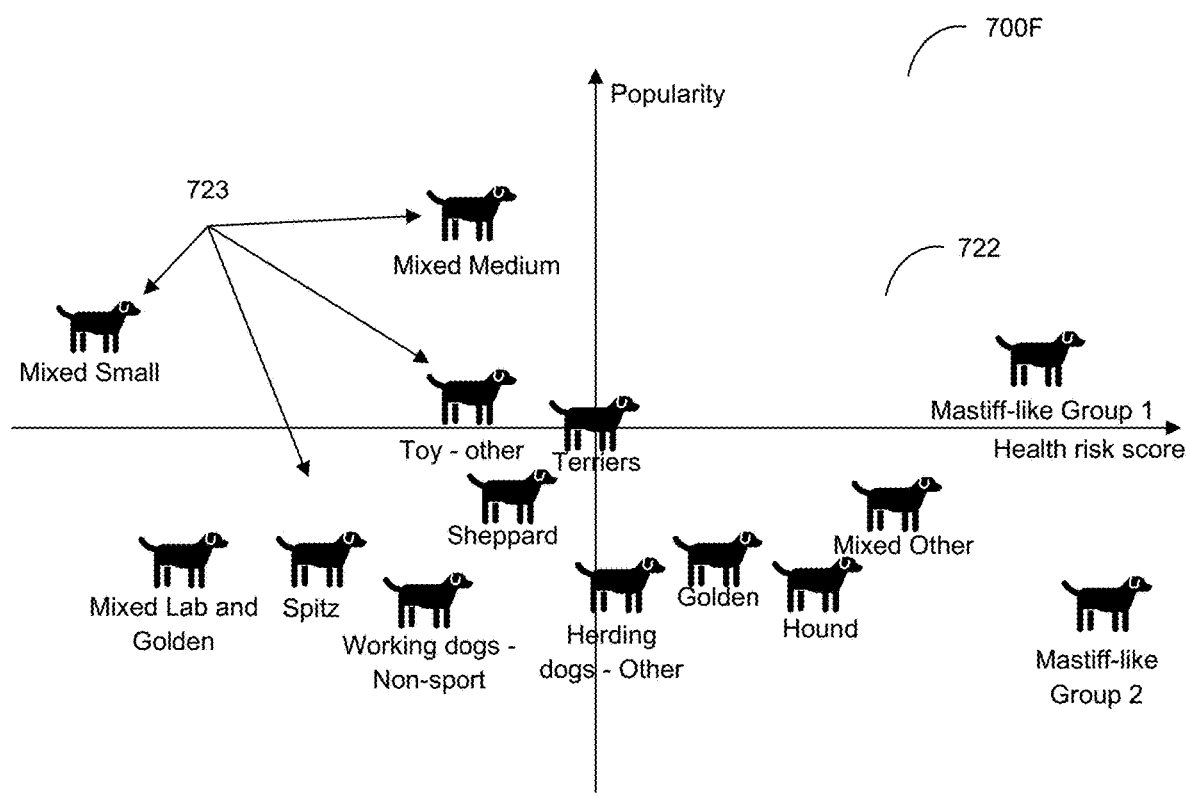

FIG. 7F depicts an illustration 700F of a scatter plot 722. The scatter plot 722 including a plurality of points 723 in the form of dog icons, where each point 723 represents a respective breed of dog. The points 723 are plotted with respect to health risk score (e.g., as determined based on simulations as discussed herein) and popularity (e.g., based on number of users having that breed of dog or otherwise based on a relative amount of people who own that breed of dog).

Figure 7G:
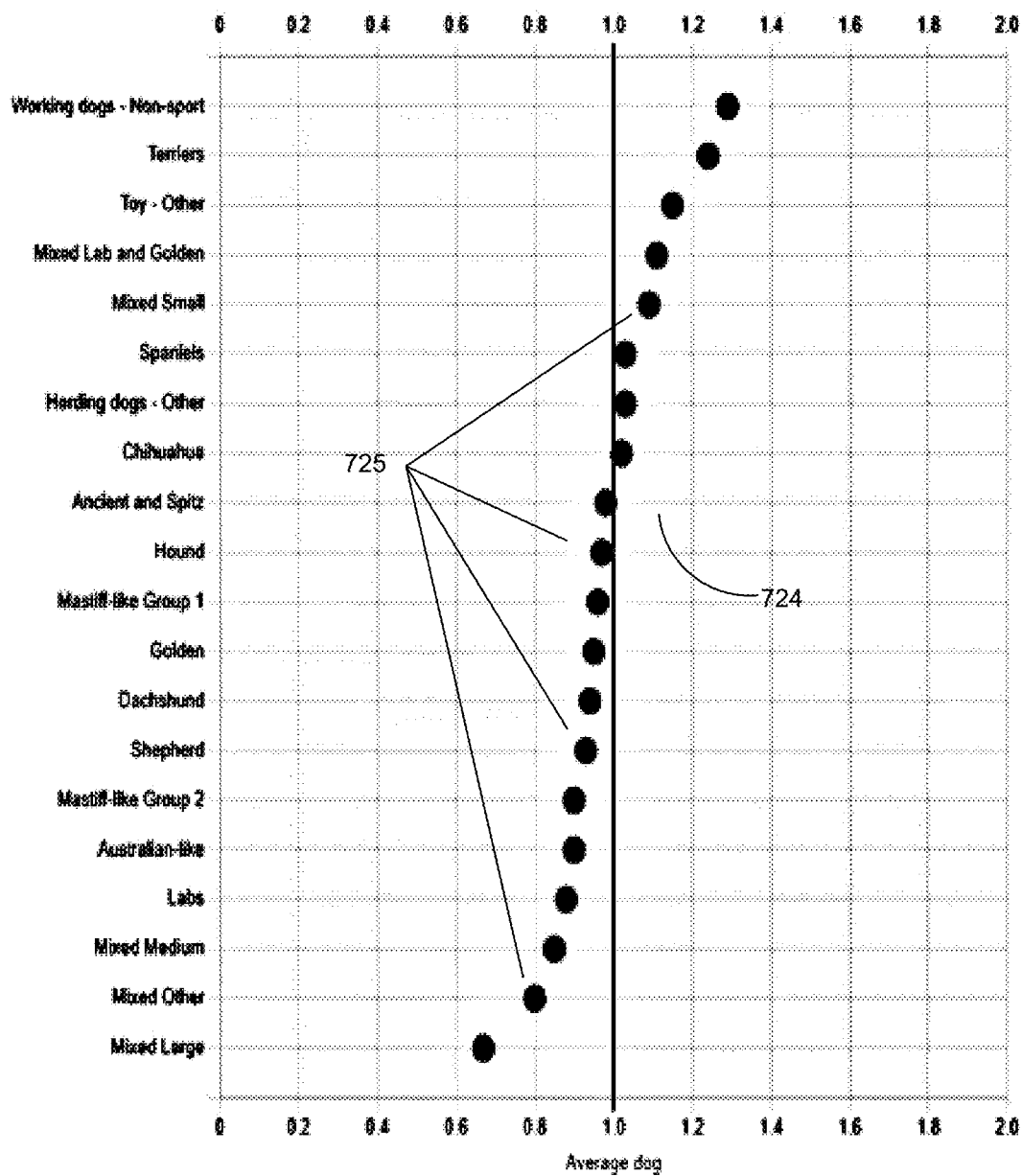

FIG. 7G depicts an illustration 700G of a scatter plot 724. The scatter plot 724 includes a series of points 725. Each of the points 725 represents a relative degree of risk of developing one or more diseases for a respective breed of dog such that the points 725 can be utilized collectively to compare disease likelihoods between dog breeds and to the average dog.

Figure 7H:
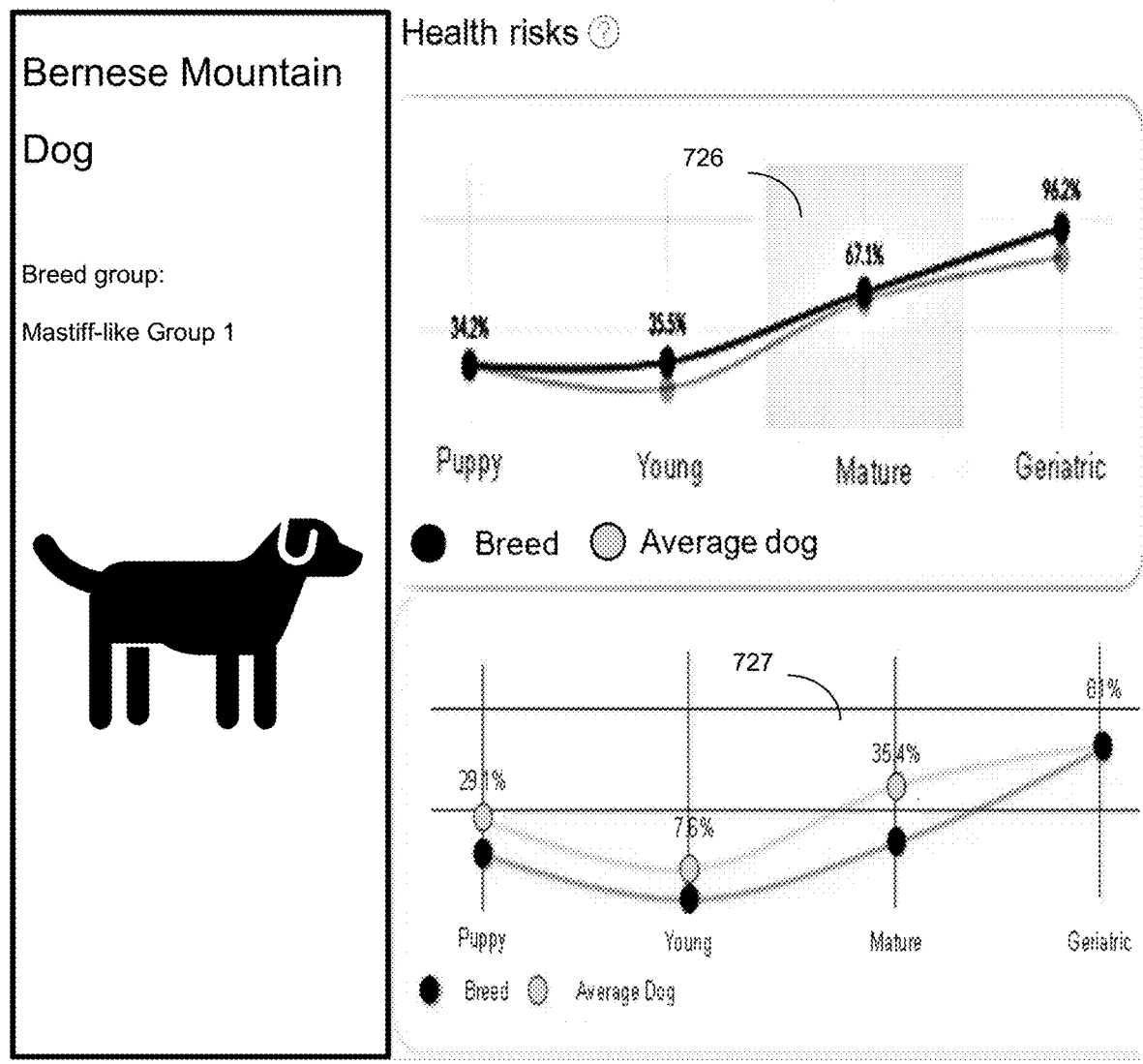
Figure 71:
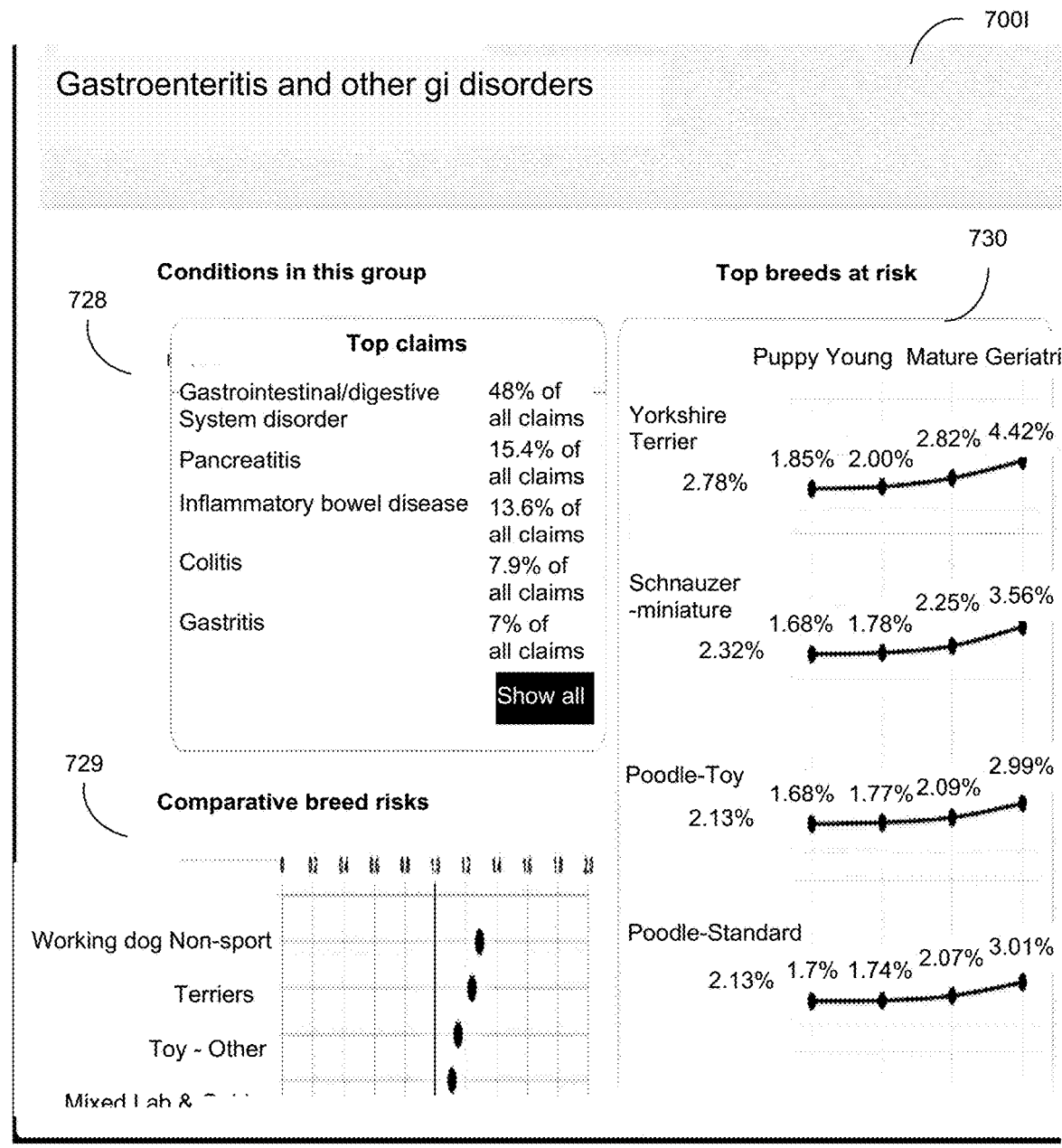

FIG. 7H depicts an illustration of a dashboard 700H. The non-limiting example dashboard 700H shows health risk and accident risk plots 726 and 727, respectively, for a particular breed of dog as compared to the average dog. As shown in FIG. 7H the dashboard 700H is for the breed "Bernese Mountain Dog" belonging to the breed group "Mastiff-like group 1." Accordingly, the simulation results based on which the plots 726 and 727 at least includes some simulations for mastiff-like dogs used to determine the breed-specific risks as well as for other breeds used to determine the average risks.

FIG. 7I depicts an illustration of a dashboard 700I. The non-limiting example dashboard 700I is generated based on simulations related to a disease group "vomiting and diarrhea," and includes various display elements 728, 729, and 730.

The display element 728 is a text box including a breakdown of different specific claims for treatment of conditions that fall under the disease group "vomiting and diarrhea."

The display element 729 includes a scatter plot with points representing relative degrees of risk of developing one or more of the diseases in the disease group "vomiting and diarrhea" for a respective breed of dog such that the points can be utilized collectively to compare likelihoods of developing a disease having conditions related to vomiting and diarrhea between dog breeds and to the average dog.

The display element 730 includes scatter plots with points representing probabilities of developing diseases related to vomiting and diarrhea at different stages of development, with each scatter plot corresponding to a respective breed or breed group. Thus, the display element 730 may be used for comparing likelihood of developing this kind of disease among dog breeds.

Figure 7J:
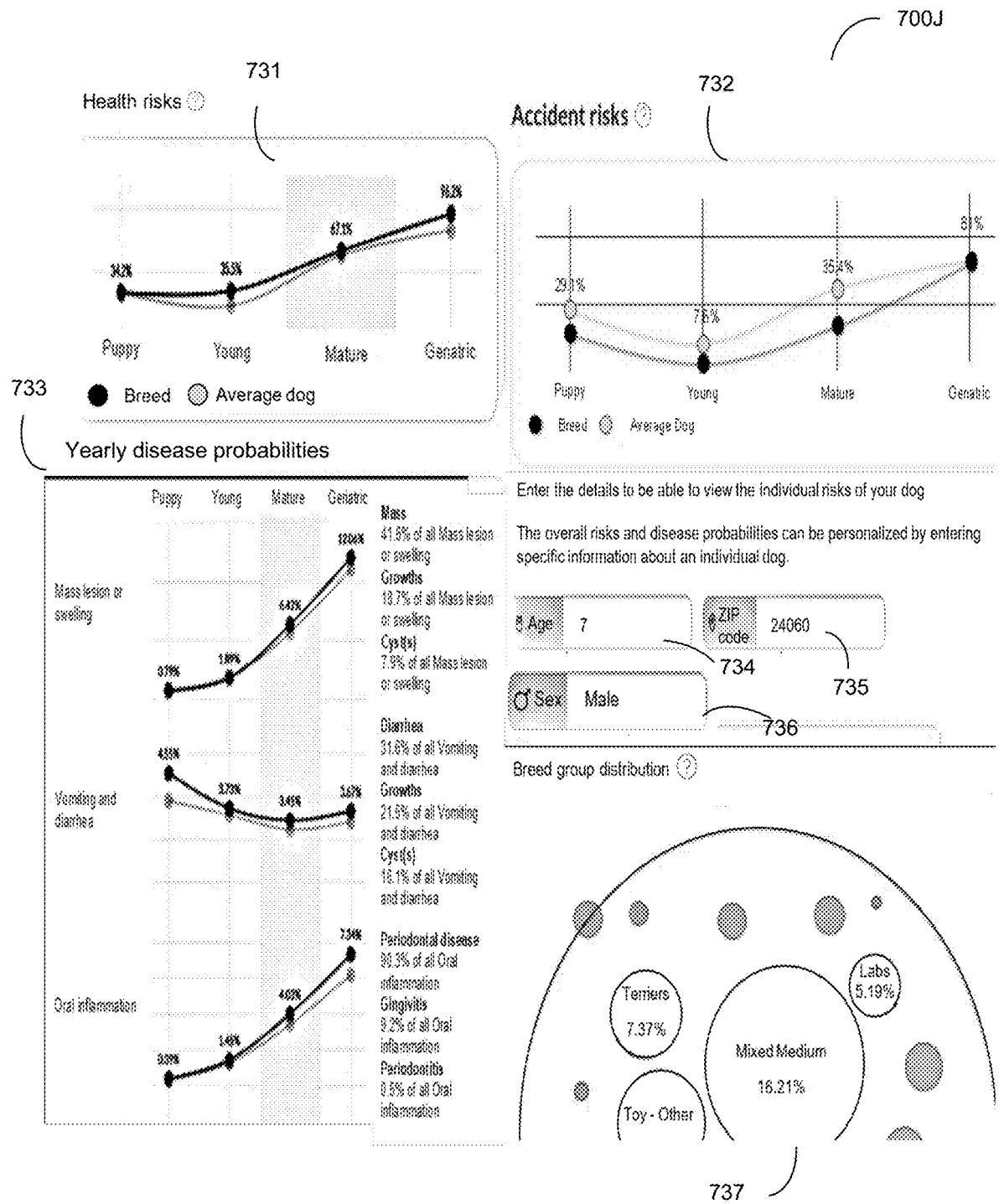

FIG. 7J depicts an illustration of a dashboard 700J including display elements 731 through 737.

The display elements 731 and 732 include sets of scatter plots representing health risks and accident risks, respectively, for a particular breed of dog as compared to the average dogs.

The display element 733 includes sets of scatter plots representing likelihoods of developing diseases for different disease groups at different stages of development for a particular breed of dog (or breed group) as compared to the average dog.

The display elements 734 through 737 are GUI fields through which a user may enter one or more respective user inputs. A breed of the dog (which may be preselected before interacting with the dashboard as shown in 700J) may be utilized in combination with one or more user inputs provided via the GUI field display elements 734 through 737 in order to determine a combination of values to be used for looking up simulation results, and simulation results associated with that combination of values may be retrieved.

The display element 737 includes a bubble chart with bubbles representing respective breeds or breed groups.

It should be noted that FIGS. 7A through 7J demonstrate non-limiting examples in which dogs are the animals whose diseases are predicted via simulations as described herein, and the illustrations visually depict potential information related to dogs. However, the disclosed embodiments are not limited to dogs, and information regarding diseases of other animals may be represented similarly to how dog disease information is presented in FIGS. 7A through 7J without departing from the scope of the disclosure. Moreover, the particular arrangements, orientations, visual representations of points, language, numbering schemes, GUI elements, or other aspects of display elements or the displays themselves are not limited as shown in FIGS. 7A through 7J.

It should also be noted that various implementations depicted in FIGS. 7A-J are described with respect to simulations results for a particular breed (or breed group), but that those implementations are not limited to breed alone. Combinations of inputs which may affect diseases or accidents (i.e., inputs to the simulations), including breed or excluding breed, may be input for a specific dog and whose data may be utilized to populate display elements as described with respect to any of FIGS. 7A-K may be equally utilized without departing from the scope of the disclosure.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for predictive disease identification, comprising:
    applying a plurality of first machine learning models based on training data in order to generate a first set of outputs, wherein the plurality of first machine learning models includes an ensemble of boosting machine learning models and a logistic regression model, wherein the ensemble of boosting machine learning models is sequentially trained using a boosting algorithm in a sequence, wherein misclassifications by a model among the ensemble of boosting machine learning models in the sequence are used to adjust weights of subsequent models among the ensemble of boosting machine learning models in the sequence;
    training a second machine learning model based on the first set of outputs, wherein the second machine learning model is a combiner model trained to output a plurality of disease predictor values based on the first set of outputs, wherein each disease predictor value corresponds to a respective disease type of a plurality of disease types, wherein each disease type of the plurality of disease types corresponds to a predetermined group of diseases;
    applying the plurality of first machine learning models and the second machine learning model based on features extracted from data including animal characteristics data of an animal, wherein outputs of the plurality of first machine learning models and the second machine learning model include a plurality of disease predictor values, wherein each disease predictor value corresponds to a respective disease type of a plurality of disease types, wherein each disease type of the plurality of disease types corresponds to a predetermined group of diseases;
    determining a plurality of simulation parameters based on the plurality of disease predictor values, wherein the plurality of simulation parameters define at least a plurality of time periods for which a plurality of disease contraction simulations are to be run;
    running the plurality of disease contraction simulations based on the plurality of simulation parameters in order to obtain simulation results, wherein running the plurality of disease contraction simulations includes providing the plurality of disease predictor values to a simulation engine configured to determine predictions of diseases for animals, wherein the plurality of disease contraction simulations are run for the plurality of time periods defined in the plurality of simulation parameters;
    generating disease contraction statistics based on the simulation results; and
    determining, based on the disease contraction statistics, at least one disease prediction for the animal.

2. The method of claim 1, further comprising:
    generating at least one insight based on the at least one disease prediction for the animal, wherein the at least one insight includes a likelihood of developing each of at least one disease at each of a plurality of stages of development of the animal.

3. The method of claim 2, wherein the plurality of stages of development of the animal includes at least one of puppy, young, mature, and geriatric.

4. The method of claim 1, further comprising:
    generating at least one insight based on the at least one disease prediction for the animal, wherein the at least one insight includes at least one expected cost of health treatment for the animal.

5. A system for predictive disease identification via simulations improved using machine learning, comprising:
    a processing circuitry; and
    a memory, the memory containing instructions that, when executed by the processing circuitry, configure the system to:
    apply a plurality of first machine learning models based on training data in order to generate a first set of outputs, wherein the plurality of first machine learning models includes an ensemble of boosting machine learning models and a logistic regression model, wherein the ensemble of boosting machine learning models is sequentially trained using a boosting algorithm in a sequence, wherein misclassifications by a model among the ensemble of boosting machine learning models in the sequence are used to adjust weights of subsequent models among the ensemble of boosting machine learning models in the sequence;
    train a second machine learning model based on the first set of outputs, wherein the second machine learning model is a combiner model trained to output a plurality of disease predictor values based on the first set of outputs, wherein each disease predictor value corresponds to a respective disease type of a plurality of disease types, wherein each disease type of the plurality of disease types corresponds to a predetermined group of diseases;
    applying the plurality of first machine learning models and the second machine learning model based on features extracted from data including animal characteristics data of an animal, wherein outputs of the the plurality of first machine learning models and the second machine learning model include a plurality of disease predictor values, wherein each disease predictor value corresponds to a respective disease type of a plurality of disease types, wherein each disease type of the plurality of disease types corresponds to a predetermined group of diseases;
    determine a plurality of simulation parameters based on the plurality of disease predictor values, wherein the plurality of simulation parameters define at least a plurality of time periods for which a plurality of disease contraction simulations are to be run;
    run the plurality of disease contraction simulations based on the plurality of simulation parameters in order to obtain simulation results, wherein running the plurality of disease contraction simulations includes providing the plurality of disease predictor values to a simulation engine configured to determine predictions of diseases for animals, wherein the plurality of disease contraction simulations are run for the plurality of time periods defined in the plurality of simulation parameters;
    generate disease contraction statistics based on the simulation results; and
    determine, based on the disease contraction statistics, at least one disease prediction for the animal.

6. The system of claim 5, wherein the system is further configured to: generate at least one insight based on the at least one disease prediction for the animal, wherein the at least one insight includes a likelihood of developing each of at least one disease at each of a plurality of stages of development of the animal.

7. The system of claim 6, wherein the plurality of stages of development of the animal includes at least one of puppy, young, mature, and geriatric.

8. The system of claim 5, wherein the system is further configured to:
generate at least one insight based on the at least one disease prediction for the animal, wherein the at least one insight includes at least one expected cost of health treatment for the animal.

9. A method for predictive disease identification, comprising:
applying a plurality of first machine learning models based on training data in order to generate a first set of outputs, wherein the plurality of first machine learning models includes an ensemble of boosting machine learning models and a logistic regression model, wherein the ensemble of boosting machine learning models is sequentially trained using a boosting algorithm in a sequence, wherein misclassifications by a model among the ensemble of boosting machine learning models in the sequence are used to adjust weights of subsequent models among the ensemble of boosting machine learning models in the sequence;
training a second machine learning model based on the first set of outputs, wherein the second machine learning model is a combiner model trained to output a plurality of disease predictor values based on the first set of outputs, wherein each disease predictor value corresponds to a respective disease type of a plurality of disease types, wherein each disease type of the plurality of disease types corresponds to a predetermined group of diseases;
applying the plurality of first machine learning models and the second machine learning model based on features extracted from data including animal characteristics data of at least one animal, wherein outputs of the plurality of first machine learning models and the second machine learning model include a plurality of disease predictor values, wherein each disease predictor value corresponds to a respective disease type of a plurality of disease types, wherein each disease type of the plurality of disease types corresponds to a predetermined group of diseases;
determining a plurality of simulation parameters based on the plurality of disease predictor values, wherein the plurality of simulation parameters define at least a plurality of time periods for which a plurality of disease contraction simulations are to be run;
running the plurality of disease contraction simulations based on the plurality of simulation parameters in order to obtain simulation results, wherein running the plurality of disease contraction simulations includes providing the plurality of disease predictor values to a simulation engine configured to determine predictions of diseases for animals, wherein the plurality of disease contraction simulations are run for the plurality of time periods defined in the plurality of simulation parameters; and
generating at least one display element based on the outputs of the the plurality of first machine learning models and the second machine learning model and the simulation results.

10. The method of claim 9, further comprising:
determining at least one disease prediction for the animal based on the outputs of the the plurality of first machine learning models and the second machine learning model, wherein the at least one display element is generated based further on the at least one disease prediction.

11. The method of claim 10, further comprising:
generating at least one insight based on the at least one disease prediction for the animal, wherein the at least one insight includes a likelihood of developing each of at least one disease at each of a plurality of stages of development of the animal.

12. The method of claim 11, wherein the plurality of stages of development of the animal includes at least one of puppy, young, mature, and geriatric.

13. The method of claim 10, further comprising:
generating at least one insight based on the at least one disease prediction for the animal, wherein the at least one insight includes at least one expected cost of health treatment for the animal.

14. A method for predictive disease identification via simulations improved using machine learning, comprising:
applying a plurality of first machine learning models based on training data in order to generate a first set of outputs, wherein the plurality of first machine learning models includes an ensemble of boosting machine learning models and a logistic regression model, wherein the ensemble of boosting machine learning models is sequentially trained using a boosting algorithm in a sequence, wherein misclassifications by a model among the ensemble of boosting machine learning models in the sequence are used to adjust weights of subsequent models among the ensemble of boosting machine learning models in the sequence;
training a second machine learning model based on the first set of outputs of wherein the second machine learning model is a combiner model trained to output a plurality of disease predictor values based on the first set of outputs, wherein each disease predictor value corresponds to a respective disease type of a plurality of disease types, wherein each disease type of the plurality of disease types corresponds to a predetermined group of diseases;
applying the plurality of first machine learning models to features extracted from data including animal characteristics of at least one animal in order to generate a second set of outputs of the plurality of first machine learning models;
applying the second machine learning model to the second set of outputs of the plurality of first machine learning models in order to output the plurality of disease predictor values;
running a plurality of disease contraction simulations based on the plurality of disease predictor values; and
generating at least one display element based on results of the plurality of disease contraction simulations.

15. The method of claim 14, further comprising:
determining at least one disease prediction for the animal based on the results of the plurality of disease contraction simulations, wherein the at least one display element is generated based further on the at least one disease prediction.

16. The method of claim 15, further comprising:
generating at least one insight based on the at least one disease prediction for the animal, wherein the at least one insight includes a likelihood of developing each of at least one disease at each of a plurality of stages of development of the animal.

17. The method of claim 16, wherein the plurality of stages of development of the animal includes at least one of puppy, young, mature, and geriatric.

18. The method of claim 15, further comprising:
generating at least one insight based on the at least one disease prediction for the animal, wherein the at least one insight includes at least one expected cost of health treatment for the animal.

19. The method of claim 14, wherein the plurality of disease predictor values is a plurality of second disease predictor values, further comprising:
applying the plurality of first machine learning models to the features extracted from the data including the animal characteristics data of the at least one animal, wherein outputs of the plurality of first machine learning models includes a plurality of first disease predictor values, wherein each first disease predictor value corresponds to a respective disease type of the plurality of disease types; and
applying the combiner model to the plurality of first disease predictor values in order to output the plurality of second disease predictor values, wherein each second disease predictor value corresponds to one of the plurality of disease types, wherein the combiner model is trained using a training data set including training outputs for the plurality of first machine learning models.

20. The method of claim 14, wherein the plurality of first machine learning models includes a boosting ensemble of sequentially applied boosting machine learning models and at least one non-boosting machine learning model.

21. The method of claim 1, further comprising:
determining a probability distribution for each of the plurality of disease types; and
creating a model of possible results for each of the plurality of disease types based on the probability distribution determined for the disease type, wherein the plurality of disease contraction simulations are run based on the model of possible results created for each of the plurality of disease types.

22. The system of claim 5, wherein the system is further configured to:
determine a probability distribution for each of the plurality of disease types; and
create a model of possible results for each of the plurality of disease types based on the probability distribution determined for the disease type, wherein the plurality of disease contraction simulations are run based on the model of possible results created for each of the plurality of disease types.

23. The method of claim 9, further comprising:
determining a probability distribution for each of the plurality of disease types; and
creating a model of possible results for each of the plurality of disease types based on the probability distribution determined for the disease type, wherein the plurality of disease contraction simulations are run based on the model of possible results created for each of the plurality of disease types.

24. The method of claim 14, further comprising:
determining a probability distribution for each of the plurality of disease types; and
creating a model of possible results for each of the plurality of disease types based on the probability distribution determined for the disease type, wherein the plurality of disease contraction simulations are run based on the model of possible results created for each of the plurality of disease types.

\* \* \* \* \*